United States Patent [19]

Rai et al.

[11] Patent Number: 5,184,190
[45] Date of Patent: Feb. 2, 1993

[54] METHOD AND APPARATUS FOR DETECTING FLAWS AND DEFECTS IN HEAT SEALS

[75] Inventors: Kula R. Rai; Thomas M. Lew; Robert B. Sinclair, all of San Antonio, Tex.

[73] Assignee: Winzen International, Inc., San Antonio, Tex.

[21] Appl. No.: 706,043

[22] Filed: May 28, 1991

[51] Int. Cl.$^5$ .................... G01N 21/88; G01N 21/89
[52] U.S. Cl. .................................. 356/239; 250/562
[58] Field of Search ............... 356/237, 239; 250/562, 250/563, 572

[56] References Cited

U.S. PATENT DOCUMENTS

| | | | |
|---|---|---|---|
| 1,763,109 | 6/1930 | Strobl. | |
| 3,656,066 | 4/1972 | Reynal | 331/65 |
| 3,754,146 | 8/1973 | Chow | 356/239 X |
| 4,110,048 | 8/1978 | Akutsu et al. | 250/563 X |
| 4,212,192 | 7/1980 | Taylor | 356/240 X |
| 4,274,748 | 6/1981 | Burtin et al. | 356/239 X |
| 4,302,106 | 11/1981 | Taylor | 356/240 |
| 4,377,341 | 3/1983 | Task et al. | 356/239 |
| 4,461,570 | 7/1984 | Task et al. | 356/239 |
| 4,647,197 | 3/1987 | Kitaya et al. | 356/239 |
| 4,679,075 | 7/1987 | Williams et al. | 356/239 X |
| 4,776,692 | 10/1988 | Kalawsky | 356/237 |
| 4,877,205 | 10/1989 | Rand | 244/31 |
| 4,993,830 | 2/1991 | Jarrett, Jr. | 356/4 |
| 5,068,799 | 11/1991 | Jarrett, Jr. | 364/507 |

OTHER PUBLICATIONS

"The Systronics Eagle" Systronics Inc, 6400 Atlantic Boulevard, Norcross, Ga.

Primary Examiner—Vincent P. McGraw
Attorney, Agent, or Firm—Michael A. O'Neil

[57] ABSTRACT

Flaws and defects in heat seals formed between sheets of translucent film are identified by optically examining consecutive lateral sections of the seal along the seal length. Each lateral seal section is illuminated and an optical sensor array detects the intensity of light transmitted through the seal section for the purpose of detecting and locating edges in the heat seal. A line profile for each consecutive seal section is derived having an amplitude proportional to the change in light intensity across the seal section. Instances in the derived line profile where the amplitude is greater than a threshold level indicate the detection of a seal edge. The detected edges in each derived line profile are then compared to a preset profile edge standard to identify the existence of a flaw or defect.

24 Claims, 15 Drawing Sheets

— dark-to-light transition
······· light-to-dark transition

— dark-to-light transition
······ light-to-dark transition

— dark-to-light transition
······ light-to-dark transition

— dark-to-light transition
······ light-to-dark transition

METHOD AND APPARATUS FOR DETECTING FLAWS AND DEFECTS IN HEAT SEALS

ORIGIN OF THE INVENTION

The invention described herein was made with Government support under contract NAS5-30856 awarded by NASA. The Government has certain rights in this invention.

TECHNICAL FIELD

The present invention relates to an apparatus for detecting the presence of flaws and defects in heat seals, and in particular to an apparatus utilizing an optical through transmission method to examine heat seals formed between sheets of plastic film for included flaws and defects.

BACKGROUND

Polyethylene based plastic films currently enjoy a wide range of uses from simple product wrapping and packaging applications to high-tech applications such as the manufacture of high-altitude balloons useful in scientific and weather data collection applications. Plastic films are generally produced by an extrusion process in which a molten resin of polyethylene or other suitable plastic material is forced through a metal die having a predetermined shape and thickness. The extruded plastic shape is typically first expanded and then cooled to set the previously molten resin in the desired shape and thickness. In order to fabricate sheets of plastic film, the molten resin is generally extruded through a circular die to form a cylindrical film. The extruded cylindrical film is first substantially expanded and is then cooled, sliced along one or both of its longitudinal edges, and finally cut transversely to form sheets having the desired dimension.

The extrusion process used to form plastic film sheets is easily adaptable to produce films in a variety of sizes, thicknesses, colors and surface finishes. Furthermore, the tensile strength and elongation properties of the extruded film may be adjusted to the user's needs by modifying the blending and alloying process used to create the molten polyethylene resin. One of the most attractive qualities of extruded plastic films is that these films can provide an air-tight and water-tight protective barrier. Thus, plastic films offer a strong, light weight, inexpensive and easily producible alternative to other protective materials and fabrics.

Many applications of polyethylene based plastic films require the joining of multiple layers, sheets or sections of plastic film. In such applications, it is often desireable to join the sheet layers by forming one or more seals between individual film sheets. One particularly effective method for forming seals between sheets of plastic film involves the application of a predetermined amount of pressure and heat to a specific sheet area to melt the sheet layers together. This method is commonly referred to as heat sealing.

The heat sealing process, if performed properly, creates an air-tight and water-tight barrier between the sealed sheets with an integrity substantially equal to, if not greater than that of the plastic film sheets from which the seal is formed. A properly formed seal also mirrors the tensile and elongation properties of the constituent film sheets that form the seal. Thus, a plurality of individual sheets properly heat sealed together perform as well as an extruded single sheet of equivalent size.

Heat seals in plastic films are generally formed by a band sealer that, through the application of heat and pressure over a narrow area in the film sheets, partially melts and fuses the sheets of plastic film together. Movement of the plastic film sheets through the band sealer creates a seal of given length and width. Flaws and defects can be encountered during the sealing process when the band sealer temperature, transitional speed or pressure varies, when the film sheets wrinkle or twist during sealing, or when foreign material is introduced into the seal. The inclusion of flaws and defects into the seal produce weak seals that may deteriorate and fail under the intended specific application. Failure of the seal can have disastrous and costly effects ranging from product spoilage or loss in packaging applications to catastrophic failure in high-tech balloon applications.

There are several types of flaws and defects commonly encountered when sheets of polyethylene film are sealed by means of a band sealer. A "tuck" or "wrinkle" flaw generally occurs when a fold in the sheet material is located in the seal. A "smear" in the seal occurs when one edge of the seal is distorted or thinned out. A "debris" defect occurs when foreign matter, for example, loose polyethylene scraps, dust or dirt, is included in the seal. A "burn" defect occurs when the band sealer temperature is too high thereby causing the seal width to shrink or creating a melt-through hole in the seal. A "cloudy" seal occurs when the seal is hazy or appears not to be sealed through all sheet layers. A "dip" or "pocket" in the seal occurs when the seal width narrows or one edge of the seal is not straight. A "cold" seal easily pulls apart, and occurs when the band sealer temperature is not high enough to sufficiently melt the film layers and form a good seal.

Historically, heat seals formed between sheets of polyethylene plastic film have been visually and manually inspected by highly trained and experienced quality control inspectors who differentiate flawed or defective seals from good seals by examining the seal for various measurable properties such as clarity, thickness, width, straightness of edge, flatness and birefringent signature. "Clarity" refers to the amount of haziness in the seal. Flaws and defects are indicated by variations in clarity, both along the seal length and across the seal width. "Thickness" is the seal dimension measured normal to the surface plane of the constituent film sheets. Variations in seal thickness are generally caused by inconsistent application of heat and pressure, by inconsistent transitional movement of the film sheets through the band sealer or by inclusion of foreign matter into the seal. "Width" is the seal dimension in the surface plane of the film sheets. Again, inconsistencies in the sealing process (heat, pressure, transition) will produce seals with width variations. "Straightness of edge" refers to whether the seal edge has a smooth, straight line or whether it is distorted or wavy in the surface plane of the film sheets along the seal length. "Flatness" refers to whether the seal will lay flat or becomes puckered or buckled when placed on a level surface. "Birefringent signature" refers to the pattern of colors exhibited by the seal area when viewed through a polariscope.

Almost all of the seal flaws and defects discussed above can be detected visually by examining the measurable properties. The exception is cold seals, which look virtually identical to good seals, but must be discovered manually by pulling on the seal. Effective and efficient quality control often requires multiple visual and manual inspections of the seal in order to guaranty its integrity. This complicated inspection process can only be accurately performed by trained and experienced inspectors and cannot be performed in real-time as the sealing process occurs. Therefore, the visual and manual inspection method is inconvenient, prohibitively costly and time consuming.

The visual and manual seal inspection and detection process is especially inconvenient, expensive and time consuming in the high-altitude balloon manufacturing industry. Inflatable balloons are generally comprised of a number of gores heat sealed together to form the balloon shape. These gores are structured of light weight, strong, non-porous, flexible extruded sheets of polyethylene film. The length of each heat seal formed between gore sheets may range anywhere from a few feet to several hundred feet long.

In common industry practice, balloons are manufactured by laying a plurality of balloon gores on a long flat table such that their common longitudinal edges are aligned. A band sealer, traveling along the common longitudinal edge to be sealed, then applies a specified amount of heat and pressure to melt and fuse adjacent gore members together. A load bearing tape (used to support the payload to be suspended under the balloon) and backup tape (used to support the seal) may also be placed along the longitudinal edge and incorporated into the seal. The sealing process is repeated for each additional gore needed to fabricate the completed balloon.

Flaws and defects are included in the heat seals formed between balloon gores when the band sealer temperature, pressure or transitional speed varies, when the film layers, load tapes or back-up tapes wrinkle, overlap, or twist, or when foreign material appears in the seal. Each of these flaws or defects may destroy the integrity of the seal rendering the fabricated balloon unusable. When possible, all detected flaws and defects are repaired. But an undetected flaw or defect could result in catastrophic balloon failure and complete loss of the balloon and its suspended payload upon inflation and launching. A finished balloon may incorporate hundreds of individual heat seals, each of which must be visually and manually inspected by the quality control inspector for flaws and defects before the balloon may be inflated. For an average size high-altitude balloon, the quality control inspectors may have to visually and manually inspect several miles of heat seals before qualifying the balloon for flight.

While reasonably efficient visual and manual inspection of heat seals can be performed by highly trained and experienced quality control personnel, this subjective approach places an enormous burden on the inspectors, provides no means of quality assurance, cannot be performed in real-time as the seals are formed and adds significantly to the balloon fabrication cost. Accordingly, there is a need for an apparatus that will reliably perform real-time inspection and examination of heat seals formed between sheets of plastic film (for example, balloon gores) to detect the presence of included flaws and defects.

SUMMARY OF THE INVENTION

The present invention overcomes the foregoing problems associated with manual and visual detection of flaws and defects included in heat seals by providing an apparatus for real-time flaw and defect detection. Manual and visual seal inspection has shown that a good seal can be differentiated from a flawed or defective seal by measuring various seal properties, such as clarity, thickness, width, straightness of edge, flatness and birefringent signature, that vary within certain limits. Variations in these measurable properties that fall outside a set of predetermined limits indicate the existence of an included flaw or defect. Unfortunately, the subjective nature of manual and visual inspection of the foregoing properties does not easily lend itself to machine recognition and flaw and defect detection.

It has been determined by examining both good and flawed seals that light transmission through a heat seal undergoes a measurable distinct attenuation, and that the amount and location of attenuation across the width of the sea differs according to the quality of the seal. Through transmitted light attenuation and its associated intensity changes across the width of a heat seal formed between sheets of translucent plastic film can be measured by a machine using optical image detection and processing for the purpose of differentiating between good and flawed or defective seals. This examination process is commonly known as optical through transmission.

The amount of light attenuation through a heat seal is a function of location across the width of the seal and the thickness of the seal. Detection of the light intensity transmitted through an individual lateral section of the heat seal can be turned into information indicating the position across the width of the seal where the through transmitted light intensity changes, for example, from dark-to-light or light-to-dark. Examination of heat seals formed by a band sealer has disclosed that severe dark-to-light and light-to-dark intensity transitions occur at points where the band sealer creates a seal edge. The existence and severity of these light intensity transitions across the lateral seal section can be detected and measured by photo sensitive optical equipment to locate seal edges formed during by the band sealing process. This image processing technique is commonly referred to as edge detection.

A comparison of good, flawed and defective seals has shown that seal quality can be determined by measuring the location, number and spacing of detected severe dark-to-light and light-to-dark transitions (edges). All heat seal flaws and defects differ from good seals and can be identified by a defect detection algorithm from the detected edge information in one of two ways: cold seals are characterized by a narrow width between seal edges, and all other seal flaws and defects were found to have extra light intensity transitions (edges) across the lateral seal section.

In accordance with the broader aspects of the present invention, the apparatus illuminates a portion of a heat seal formed between a number of sheets of translucent plastic film. An optical sensor array examines consecutive illuminated lateral sections of the heat seal along the seal length to detect the intensity of light transmitted through each consecutive lateral seal section. A dedicated electronic circuit connected to the optical sensor array processes the detected through transmitted light intensity to locate light-to-dark and dark-to-light transitions across the lateral seal section by means of an edge detection algorithm. A line profile of the through transmitted light intensity transitions across the scanned lateral section is generated by the edge detection algorithm for each section. The amplitude of the generated line profile is interpreted by the circuit to detect the location, across the width of the lateral section, of all edges formed by the band sealer.

The electronic circuit differentiates good seals from flawed or defective seals by executing a flaw detection algorithm that calculates seal width from the detected seal edges and searches for the presence of extra seal edges. Detected seal widths less than a predetermined minimum indicate the existence of a cold seal, and the detection of extra seal edges indicates the presence of all other identified types of seal flaws or defects. In each case, the apparatus of the present invention will mark the location on the seal where the flaw or defect was discovered for further manual inspection and, if possible, repair.

The heat seal flaw and defect detector of the present invention may be adapted to examine any heat seal formed between sheets of plastic film for included flaws and defects. Other advantages and applications deriving from the use of the invention will readily suggest themselves from those skilled in the art upon consideration of the following Detailed Description taken in conjunction with the accompanying Drawings.

BRIEF DESCRIPTION OF THE DRAWINGS

A more complete understanding of the invention may be had by reference by the following Detailed Description when taken in conjunction with the accompanying Drawings, wherein.

DETAILED DESCRIPTION OF THE DRAWINGS

Although the present invention will be described herein in terms of its preferred application as an apparatus for detecting flaws and defects in heat seals formed between balloon gores, it will be understood that the apparatus of the present invention is not so limited in application and may be utilized to detect flaws and defects in any heat seal formed between sheets of translucent film.

Figure 1:
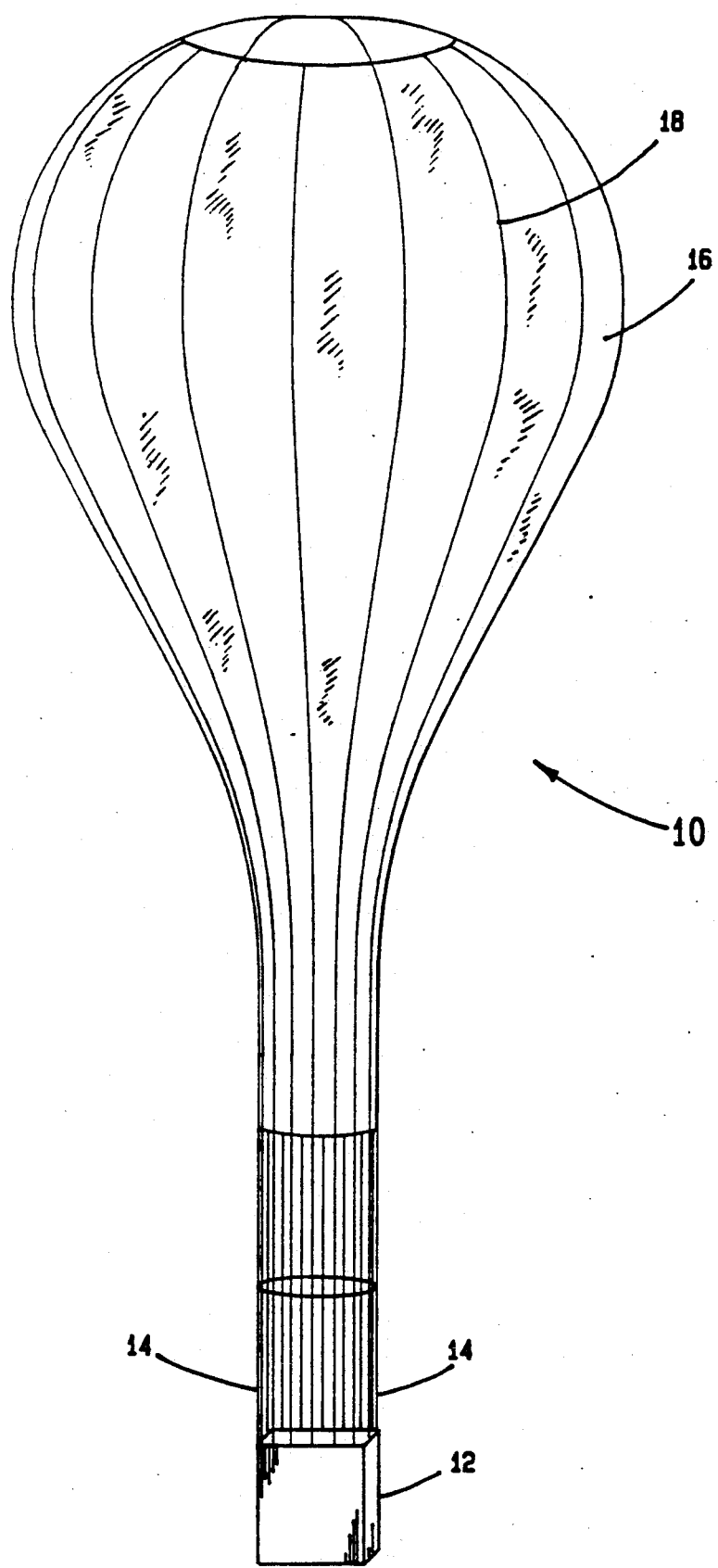
FIG. 1 shows a high-altitude scientific balloon manufactured by heat sealing a plurality of plastic film gores.

Referring now to FIG. 1, there is shown a high-altitude balloon 10 supporting a suspended payload 12. The payload 12 may comprise, for example, a sophisticated data collection apparatus useful in scientific and/or weather forecasting applications. The payload 12 is attached to the balloon 10 by means of a plurality of load wires 14. The balloon 10 is comprised of a number of gores 16 attached together side-by-side. A typical balloon is comprised of many gores.

Each gore 16 is structured of a light weight, strong, non-porous, flexible sheet of translucent polyethylene film. An example of such a material is STRATOFILM (a registered trademark of Winzen International, Inc.), which is specifically developed for large high-altitude balloons and is made from an extruded low-density polyethylene polymer. The balloon 10 is fabricated by sequentially fusing adjacent gores 16 together by means of a heat sealing process to be described. Each gore 16 incorporated into the balloon 10 may comprise one or more sheets of translucent polyethylene film.

The sealing process between adjacent gore sheets 16 creates an air-tight and water-tight seal 18. Load bearing tapes 19 may also be sealed to the balloon at each seal 18. Inclusion of load tapes 19 reduces stretching of the gore material by the weight of the included payload 12. After the first seal 18 is formed, the fused adjacent gores 16 are oriented to accept another adjacent gore. This sequential sealing process is repeated until enough adjacent gores have been sealed together to form the desired balloon envelope. Both the shape of the balloon (envelope) and the load bearing tapes 19 serve to distribute and carry the weight of any payload 12 that may be suspended under the balloon 10.

Figure 2:
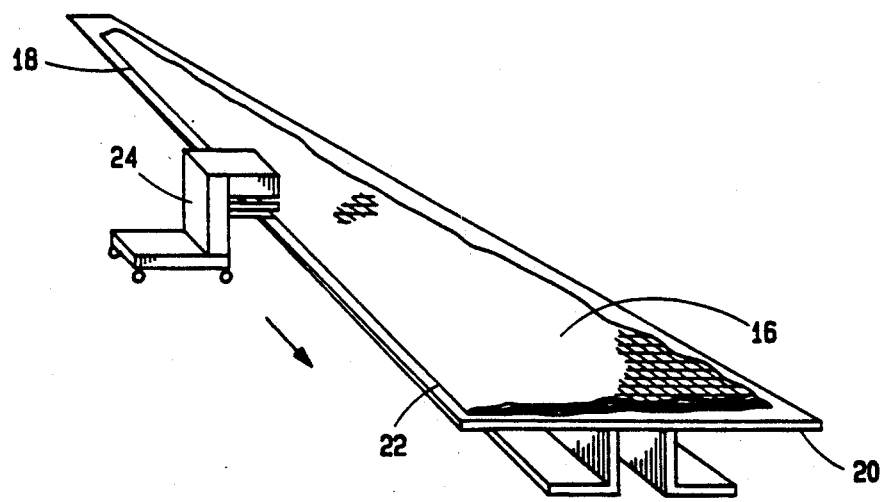
FIG. 2 is a perspective view showing the process for sealing adjacent balloon gores.
Figure 3:
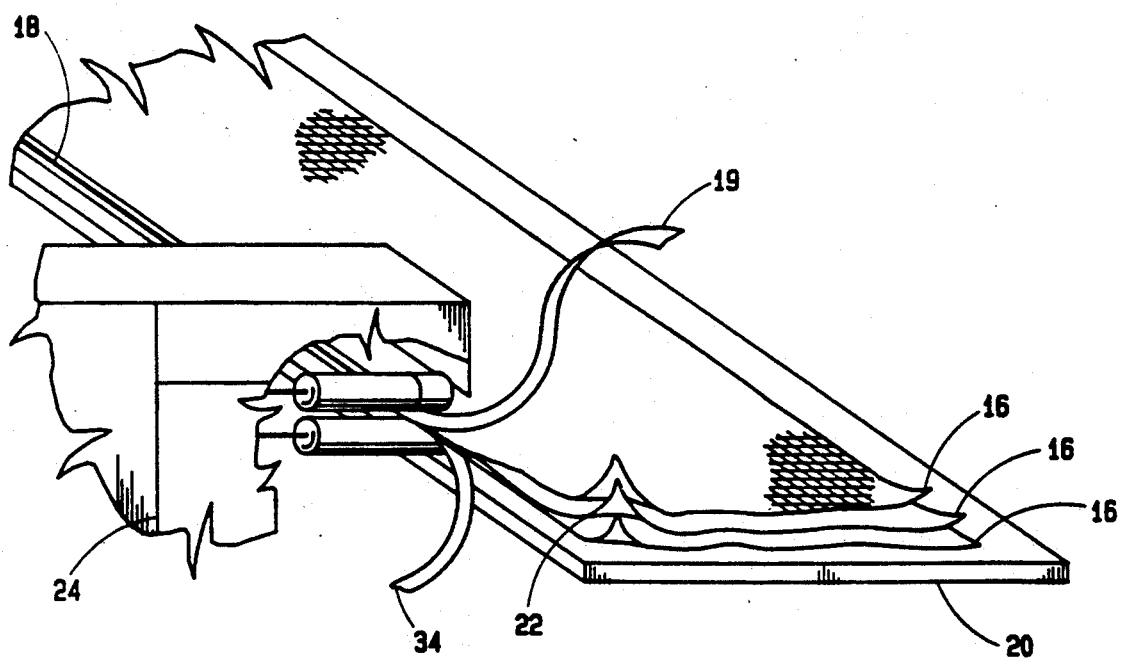
FIG. 3 is a perspective view of the band sealer used in the heat sealing process.

Referring now to FIGS. 2 and 3, there is shown the heat sealing process for sequentially fusing adjacent gores 16 together to form the balloon. According to the preferred practice, two or more gores 16 are laid on a long flat table 20 such that their common longitudinal edges 22 are aligned. A band sealer 24, traveling along the common longitudinal edge 22 to be sealed, applies a specified amount of heat and pressure to a small area along the edge to melt and fuse adjacent gores 16 together thereby forming the air-tight and water-tight seal 18. The load bearing tape 19 used to support the suspended payload 12 (FIG. 1) and a backup tape 34 used to support the seal may be placed along the longitudinal edge 22 and incorporated into the seal 18 by the band sealer 24.

Flaws and defects in the seal 18 formed by the band sealer 24 can be introduced when the band sealer pressure, temperature or transitional speed along the seal edge varies, the gore sheets 16 or tapes, 19 and 34, fold or wrinkle in the seal or when any foreign matter or debris is introduced into the seal. Flaws and defects formed in the seal 18 by the heat sealing process produce weak seals that may deteriorate and fail under tension, pressure or temperature.

Figure 4A:
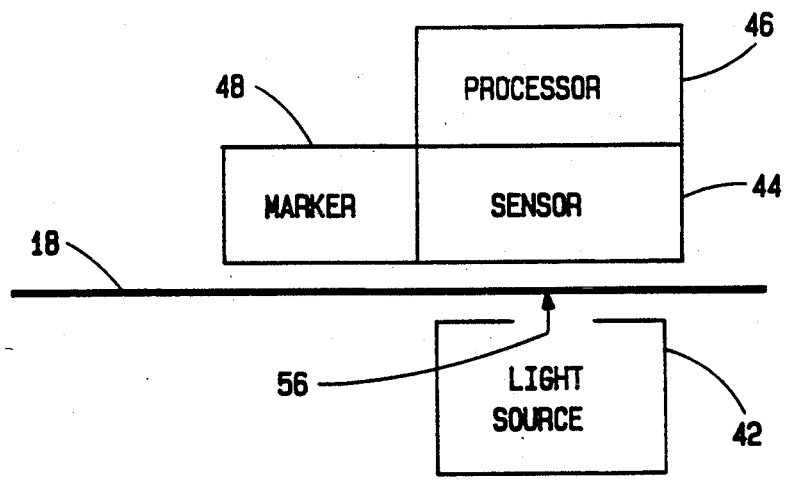
FIG. 4A is a side view block diagram of the seal inspection apparatus of the present invention.
Figure 4C:
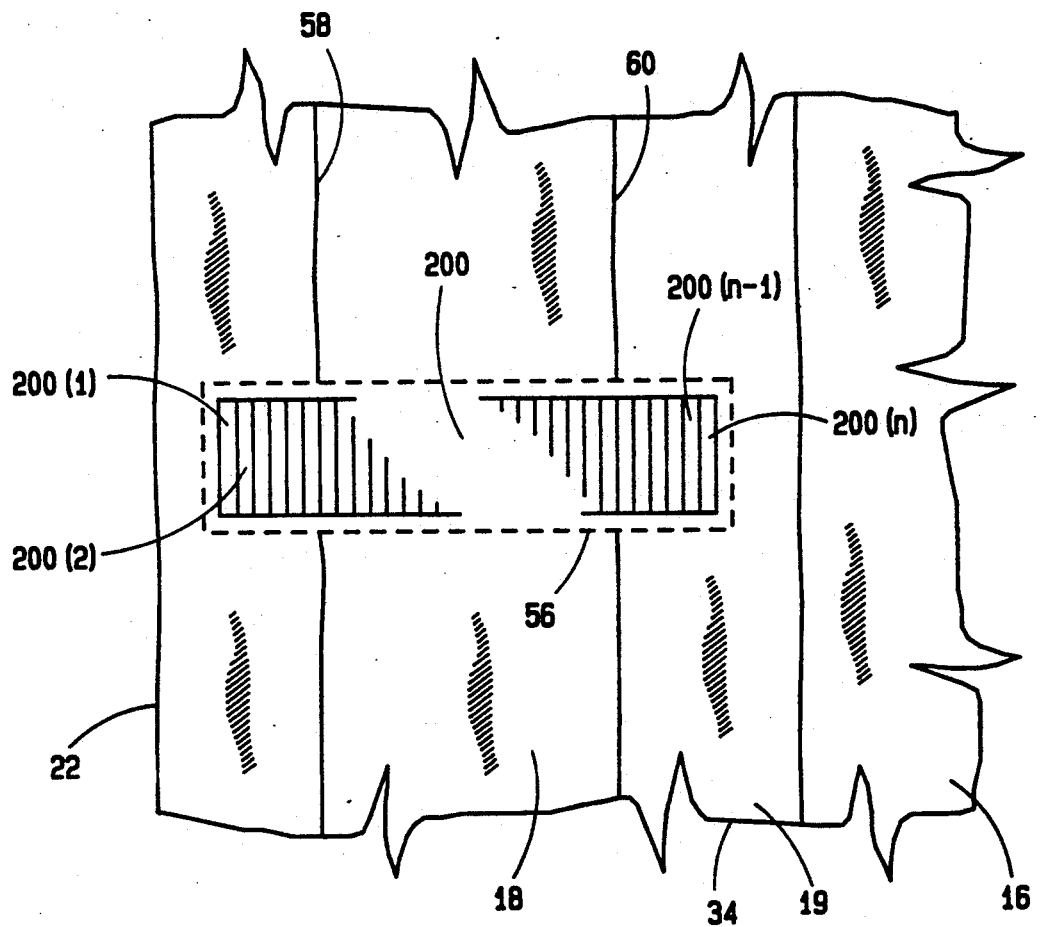
FIG. 4C shows the pixel division of the scanned lateral seal section by the apparatus for performance of digital image processing.
Figure 4B:
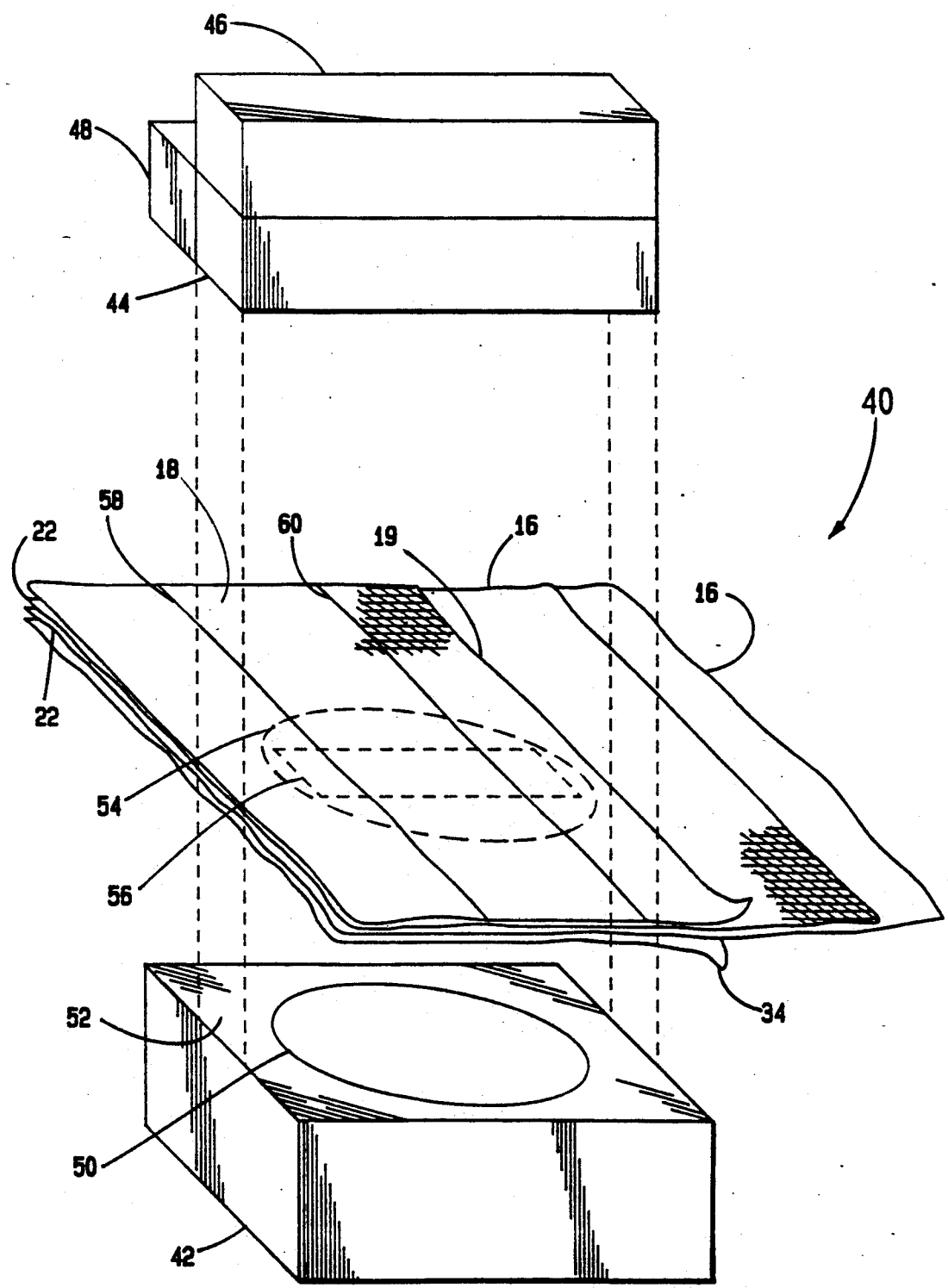
FIG. 4B is an exploded perspective view of the seal inspection apparatus as shown in FIG. 4A.

Reference is now made to FIGS. 4A and 4B wherein FIG. 4A is a side block diagram, and FIG. 4B is an exploded perspective view of the apparatus 40 for detecting the presence of flaws and defects in heat seals 18 comprising the present invention. The apparatus 40 includes an illuminator 42, an optical sensor 44, a dedicated image processor 46 and a flaw marker 48. Contained within the illuminator 42 is a light source that is preferably a steady, non-flickering white light, but may alternatively be either a laser light or an infrared source. An opening 50 in the top 52 of the illuminator 42 allows for radiant energy from the light source to be emitted.

The illuminator 42 is advantageously positioned under the heat seal 18 to be examined for flaws and defects such that the emitted radiant energy from the light source illuminates a portion of the seal as generally indicated by broken line 54 in FIG. 4B. An optical sensor 44 is placed on the opposite side of the heat seal 18 such that the seal is positioned between the sensor 44 and the illuminator 42. Orientation of the illuminator 42, seal 18 and sensor 44 in this manner enables the sensor 44 to detect the intensity of light transmitted through the seal. This process is commonly referred to as optical through transmission. Optical sensor 44 detects and converts through transmitted light intensity across the width of the seal 18 into proportional electrical signals that are processed by image processor 46 using a method to be described to detect the presence of flaws and defects. Upon detection of a flaw or defect, processor 46 signals the flaw marker 48 to physically tab and/or store the location of the lateral seal section 56 containing the flaw for further processing and review.

In detecting the through transmitted light intensity, the sensor 44 examines the illuminated lateral section of the seal, as generally indicated by broken line 56 in FIG. 4B, that includes the complete width of the seal 18 and a portion of the gores 16 and tapes, 19 and 34, on each side of the opposed edges, 58 and 60 respectively, of the seal 18. Light transmission through the heat seal undergoes a measurable distinct attenuation creating intensity transitions, for example, from light-to-dark and dark-to-light, across the seal section 56. The image processor 46 locates and identifies flaws and defects in the lateral seal section 56 by first executing an edge detection algorithm that processes the optically through transmitted light intensities detected by the sensor 44 to detect and chart the position of intensity transitions across the seal section 56. Locations across the seal section 56 where severe light intensity transitions occur are labeled by the edge detection algorithm as seal edges. A defect detection algorithm executed by the processor 46 then characterizes good, flawed and defective seals by comparing the location, number, spacing of and distance between these identified light intensity transition (edges) to a preset edge standard. In determining whether a defect is included in the seal section 56, the defect detection algorithm characterizes cold seals by the detection of a narrow seal width and all other seal flaws and defects for detection of more than two significant edges, 58 and 60.

Reference is now made to FIG. 4C for a description of the manner in which the apparatus 40 (FIGS. 4A and 4B) detects seal edges. The edge detection algorithm executed by the image processor 46 (FIGS. 4A and 4B) performs digital image processing on each examined lateral seal section 56 to determine the existence and location of seal edges. For digital image processing, the lateral seal section is evenly divided into a linear series of small regions 200. Four representative regions, labeled as 200(1), 200(2), 200(n-1) and 200(n), are shown in FIG. 4C within the examined lateral section 56. The outputs of the sensor for each small region 200 are commonly referred to as pixels, or picture elements.

The optical sensor 42 (FIGS. 4A and 4B) samples and quantizes the through transmitted image brightness (light intensity) for each pixel 200 and generates an analog signal for each examined pixel having an amplitude proportional to the detected image brightness. An analog-to-digital converter within the image processor converts each analog signal to an integer value that represents the brightness or darkness (through transmitted light intensity) of each pixel across the examined lateral section 56. The integer values are stored in a one-dimensional array of length n corresponding to the number of pixels 200(n) examined across the lateral section 56.

The edge detection algorithm executed by the image processor uses the one-dimensional image brightness data array as input to generate a line profile for the examined lateral section 56. The line profile generated by the edge detection algorithm is comprised of a number of spikes whose position on the horizontal axis of the profile corresponds to the location across the seal section where image intensity contrasts occur. The amplitude of the line profile is proportional to the change in light intensity across the lateral section 56. The change in light intensity across the seal section is determined by comparing, starting with the first pixel 200(1), the detected image brightness between adjacent pixels. For example, the algorithm calculates the difference in image intensities (contrasts) between pixels 200(1) and 200(2) and generates a peak in the profile having an amplitude proportional to the difference in detected image intensity Severe light-to-dark or dark-to-light image intensity transitions create a high amplitude spike in the generated line profile, and a gradual intensity change generates a gradual change of nominal amplitude. The comparison process is consecutively repeated for each pixel 200 across the examined lateral section 56 until pixel 200(n−1) is compared to the last pixel 200(n).

The edge detection algorithm differentiates between and identifies light-to-dark and dark-to-light intensity transitions (spikes) in the line profile and completes the detection process by identifying seal edges. Seal edges are detected by establishing a line profile reference edge amplitude (threshold). Any generated spike, either light-to-dark or dark-to-light, having an amplitude greater than threshold level is labeled by the algorithm as being indicative of the presence of a detected seal edge.

Figure 5:
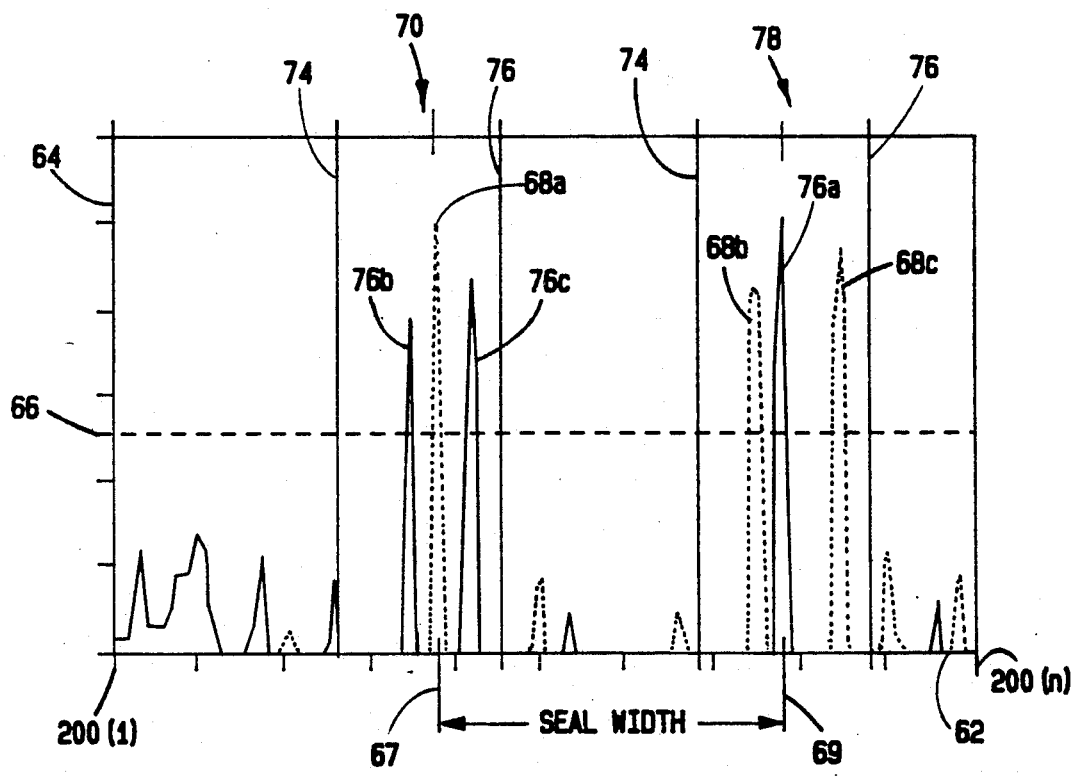
FIG. 5 shows a characteristic line profile for a good seal as generated by the heat seal inspection apparatus of the present invention.
Figure 6:
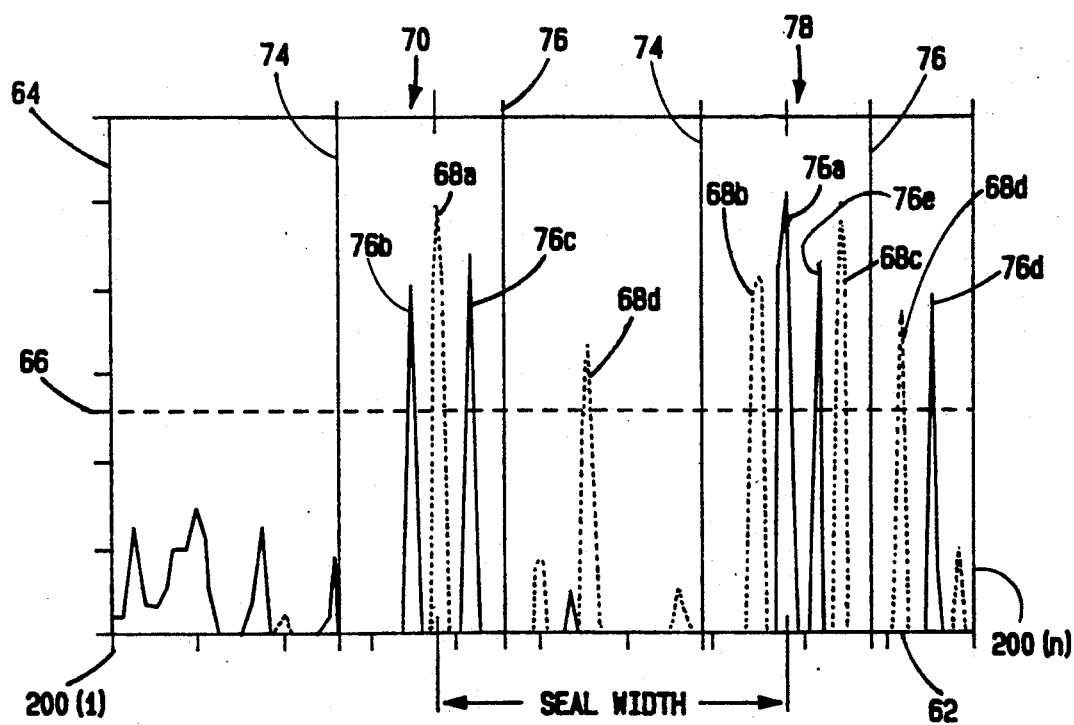
FIG. 6 shows a characteristic line profile for a flawed or defective seal as generated by the heat seal inspection apparatus of the present invention.

Reference is now made to FIGS. 5 and 6, wherein FIG. 5 shows a characteristic line profile generated by the image processing edge detection algorithm for a good seal, and FIG. 6 shows a characteristic line profile for a flawed or defective seal. For each line profile, the horizontal axis 62 defines the distance across a lateral seal section 56 between pixels 200(1) and 200(n), and the vertical axis 64 represents the change of light intensity transitions (contrasts) between adjacently compared pixel elements. A threshold intensity level 66 is also established on the vertical axis 64 to assist in detecting seal edges. Any generated spike having an amplitude less than the threshold level 66 is ignored by the algorithm, while spikes with amplitudes greater than the threshold are labeled "significant" and indicate the detection of a seal edge formed by the heat sealer.

After the edge detection algorithm generates the line profile for the seal section 56, the image processor executes the defect detection algorithm to compare the generated line profile to the preset profile standard to detect the existence of flaws and defects. FIG. 5 shows the expected line profile generated by the edge detection algorithm for a good seal. In executing the defect detection algorithm, the image processor, starting at pixel location 200(1) at the left hand side of the line profile, searches for the first significant light-to-dark spike 68a in the generated line profile. This spike, 68a, is labeled as the top edge 67 of the seal. An area 70 is established identifying the width of the top edge of the seal. Area 70 is centered around the top edge spike 68a and defined by seal edge area lines 74 and 76. The processor next searches for the first significant dark-to-light spike 76a in the generated line profile to the right of spike 68a and outside the defined top edge area 70. This spike, 76a, is labeled as the bottom edge 69 of the seal. A bottom edge seal area 78 identifying the width of the bottom edge of the seal is also established similarly to area 70, bottom edge are 78 is centered around bottom edge spike 76a and further defined by edge lines 74 and 76.

The width of the seal under examination is defined to be the distance in pixels between the first significant light-to-dark spike 68a, indicating the location of the top edge 67, and the first significant dark-to-light spike 70a, indicating the location of the bottom edge 69 of the seal. Any additional significant light-to-dark and dark-to-light spikes (for example, 68b, 68c, 76b and 76c) detected by the algorithm may also be present in the line profile but are ignored by the defect detection algorithm provided that they lie within the defined seal edge areas 70 and 78.

Referring now to FIG. 6, the characteristic line profile generated for a flawed or defective seal shows the detection of significant transition spikes (68a and 76a) and ignored spikes (68b, 68c, 76b and 76c) as in FIG. 5, but further identifies the presence of additional unwanted spikes indicating the inclusion of a flaw in the seal. For example, additional significant spikes 68d and 76d are detected outside the defined top and bottom edge areas 70 and 78. Furthermore, an additional significant dark-to-light spike 76e has been detected within edge area 78 near the significant dark-to-light bottom edge spike 76a (double spiking).

Flawed or defective seals are generally characterized by either the absence of seal edge spikes 68a and 76a, the presence of additional unwanted spikes, like 68d, 76d and 76e, or the phenomenon of spikes 68a and 76a being too close together (narrow seal width). In conclusion, the defect detection algorithm identifies included flaws in the heat seal by detecting seal edges denoted by spikes 68a and 76a, performing a minimal width check (normally the equivalent of one-eight of an inch in pixels) between the top edge 67 and the bottom edge 69, disregarding additional spikes within seal areas 70 and 78, if present, and searching for extra significant spikes outside the seal areas or double spikes within the seal areas.

Figure 7A:
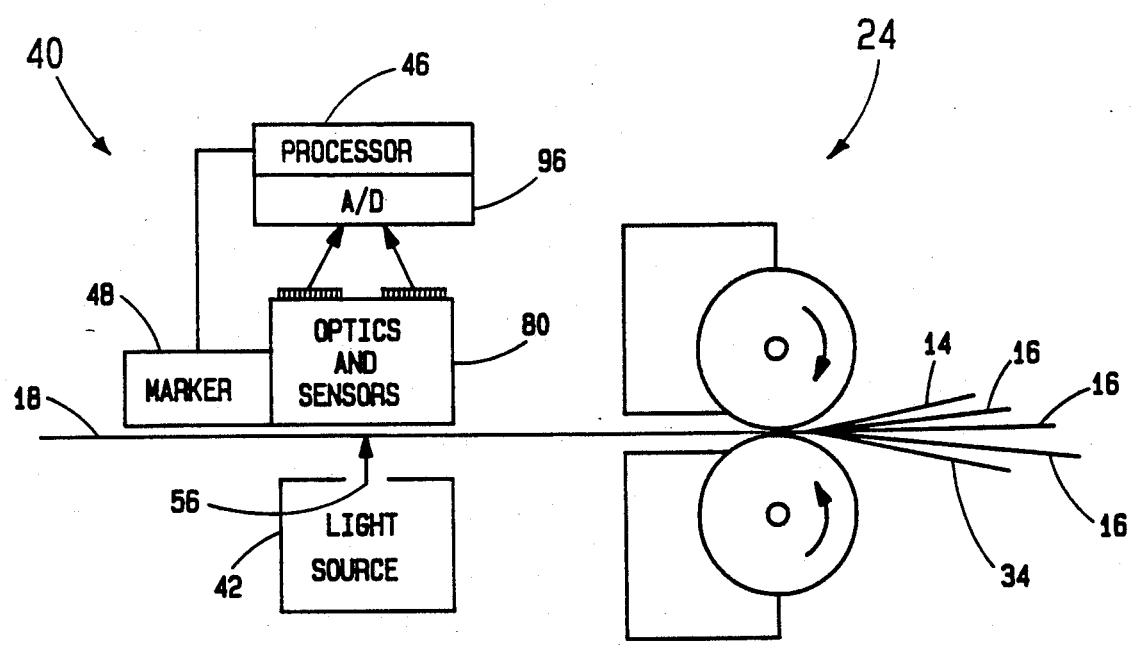
FIG. 7A is a side view block diagram for one embodiment of flaw detection apparatus of the present invention.
Figure 7B:
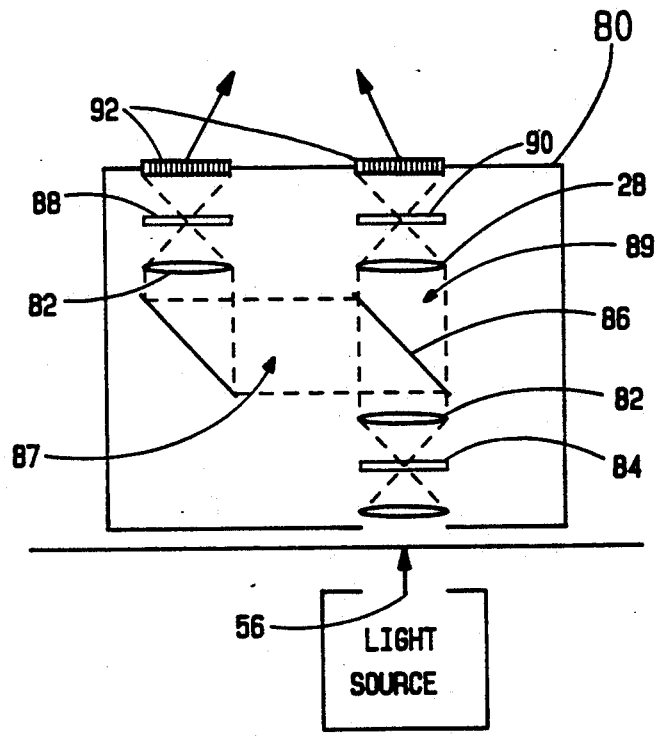
FIG. 7B is a diagram of the optics and sensor portion of the apparatus as shown in FIG. 7A.

Referring now to FIGS. 7A and 7B, there is shown one embodiment for the apparatus 40 as shown in FIGS. 4A and 4B to detect the presence of flaws and defects in heat seals 18 formed between sheets of translucent plastic film. Light emitted from the illuminator 42 is directed through a lateral section 56 of the seal 18 to an optics and sensor component 80 that detects the through transmitted light intensity.

The optics and sensor component 80 contains a number of focusing convex lenses 82. Within the optics and sensor component 80, the through transmitted light image is first blurred by passing it through a low pass spatial filter 84. This process eliminates image noise without affecting the visibility of any included flaws. The image is then separated into two components by means of a two-way mirror 86. The first image component 87 is passed through a light-to-dark edge enhancing filter 88 to a first photo electric sensor array 92. The second image component 89 is passed through a dark-to-light edge enhancing filter 90 to a second photoelectric sensor array 94.

The photo sensor arrays, 92 and 94, examine a defined pixel array and detect light intensity transmissions across the seal section 56. Light intensity signals generated by the photo sensor arrays 92 and 94 are digitized by an analog-to-digital converter 96 and processed by the image processor 46. The edge detection algorithm executed by the processor 46 generates a line profile showing the occurrence of light intensity transitions across the examined seal section 56. The processor 46 further executes the defect detection algorithm to compare the generated line profile with a preset profile standard to identify flaws and defects within the seal 18. Upon detection of a flaw or defect, processor 46 signals flaw marker 48 to tab and/or record the location of the seal section containing the detected flaw or defect.

Figure 8A:
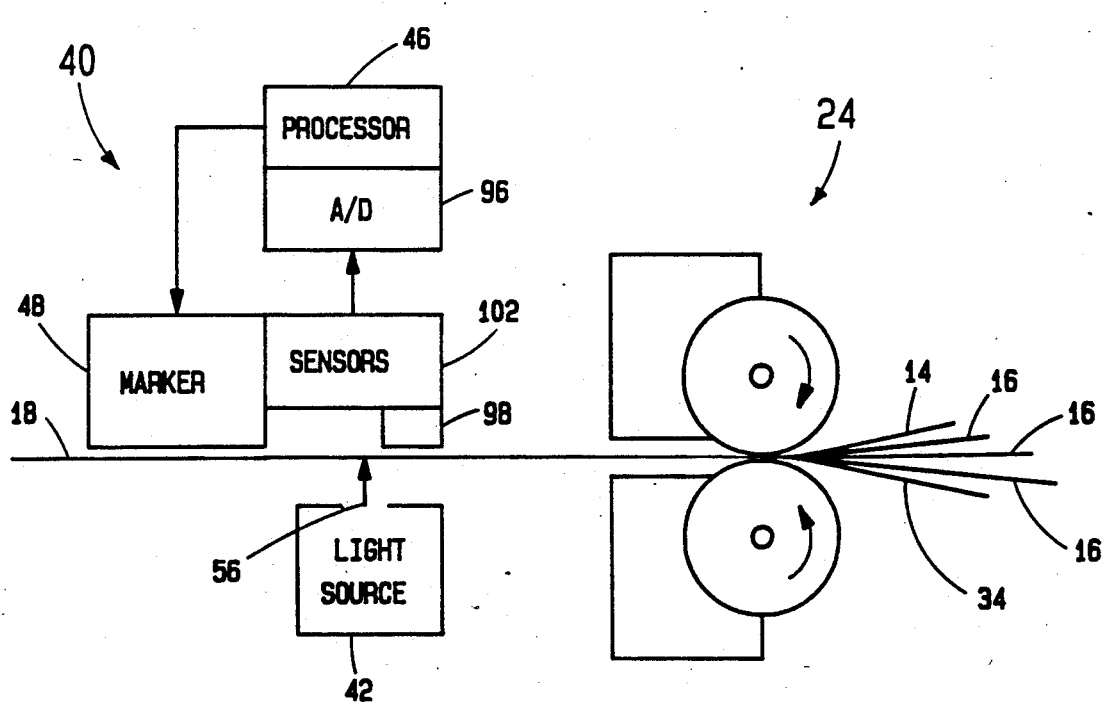
FIG. 8A is a side view block diagram for a second embodiment of the flaw detection apparatus of the present invention.
Figure 8B:
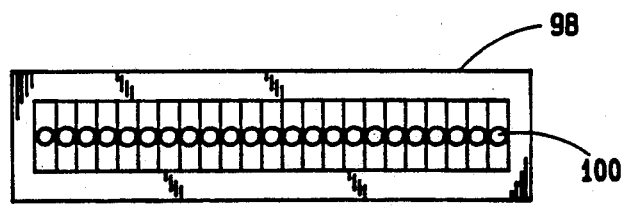
FIG. 8B is a bottom view of the fiber optic detector network of the apparatus as shown in FIG. 8A.

Referring now to FIGS. 8A and 8B, there is shown a second embodiment for the apparatus 40 as shown in FIGS. 4A and 4B to detect the presence of flaws and defects in heat seals 18 formed between translucent sheets of plastic film. The illuminator 42 shines light through a lateral section 56 of the seal 18 to a fiber optic detector array 98. The fiber optic detector 98 is comprised of a plurality of fiber optic cables 100 arranged in a linear array and oriented such that the detector 98 extends transversely across the complete width of the seal, parallel to and coplanar with the lateral seal section 56 under examination. The fiber optic cables 100 are coupled on a one-to-one basis to a plurality of photoelectric sensors 102 that generate electrical signals having amplitudes proportional to the detected through transmitted light intensity. It will be understood that any sensitive photoelectric sensor array can be substituted for the fiber optic detector 98. Output signals from the sensors 102 are converted into digital signals by an analog-to-digital converter 96 and processed by the image processor 46 in the manner previously described to generate line profiles, detect included flaws and defects and tab and record flaw locations.

Figure 9A:
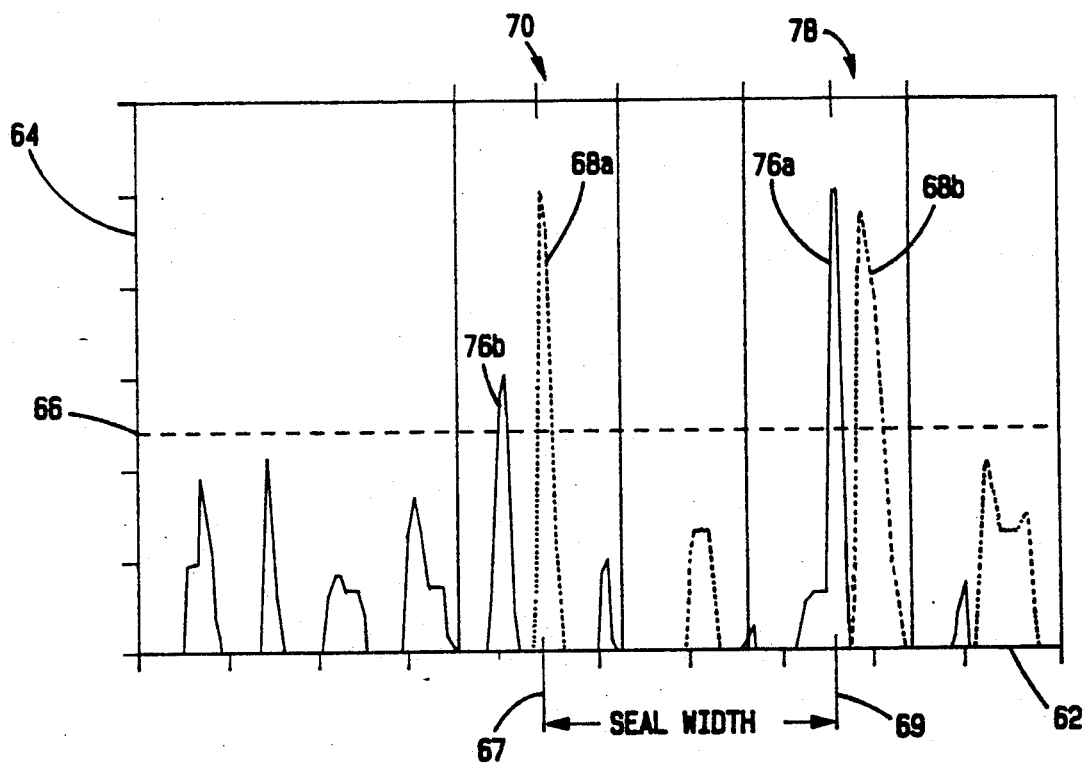
FIGS. 9A-9D show actual line profiles generated by the apparatus of the present invention showing a variety of good seals.
Figure 9B:
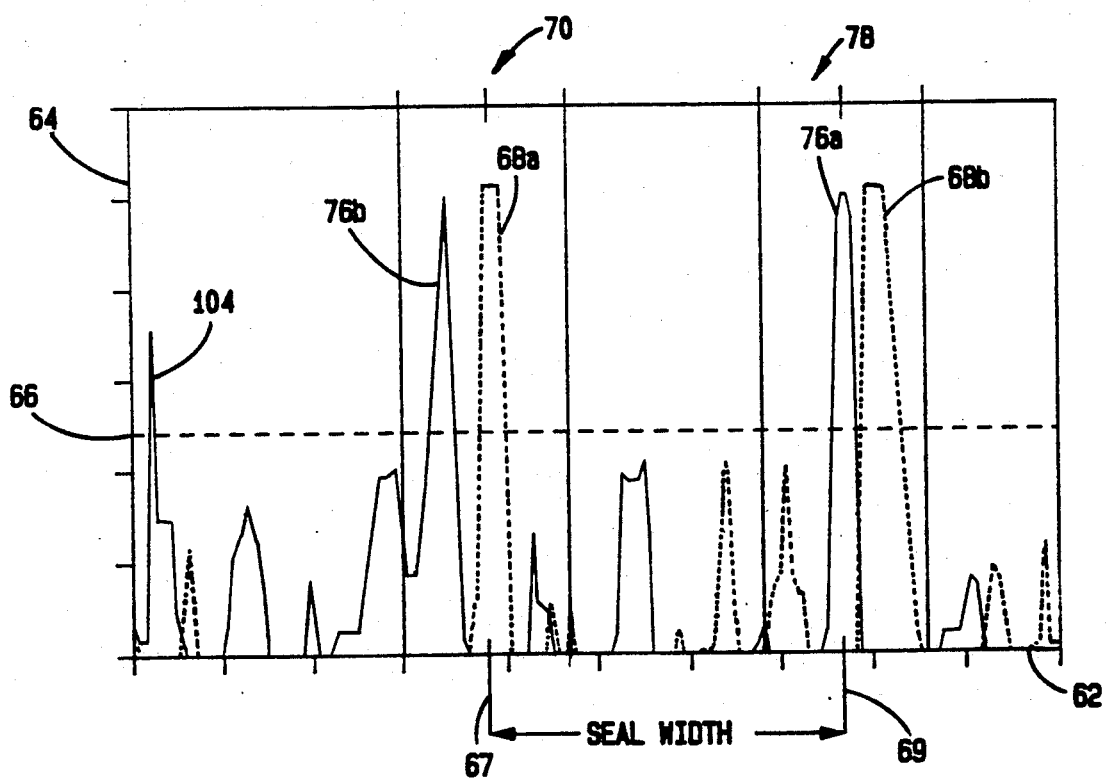
Figure 9C:
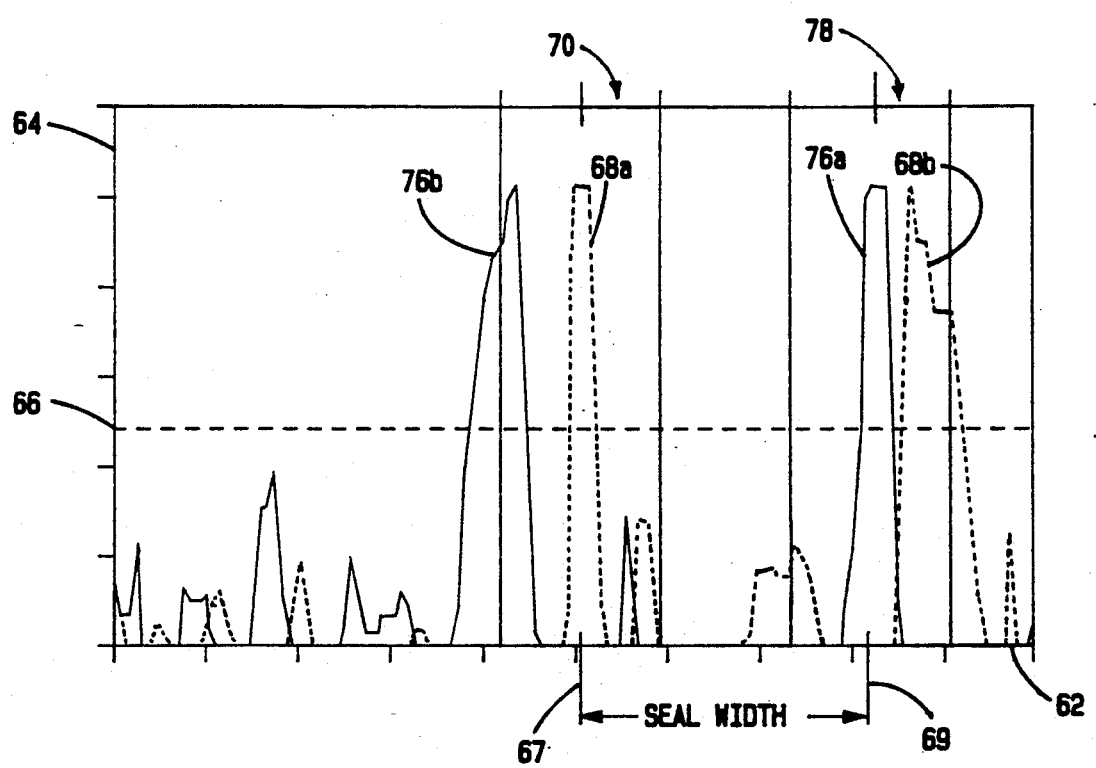
Figure 9D:
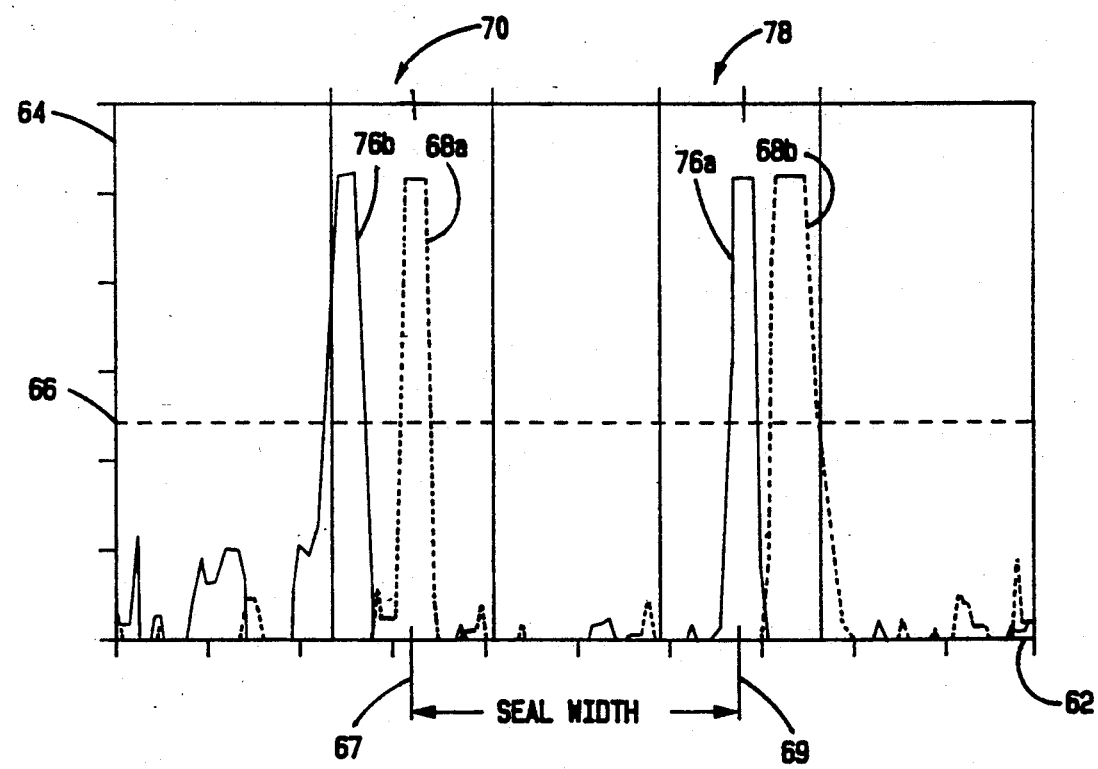

Referring now to FIGS. 9A-9D, there are shown several actual line profiles generated by the apparatus 40 for a variety of good seals. In each figure, the edge detection algorithm has located the top and bottom seal edges, 67 and 69 respectively, denoted by spikes 68a and 76a, and the defect detection algorithm has calculated the seal width between edge locations 67 and 69 to be within the minimum range. Additional spikes 68b and 76b are disregarded because they are positioned within seal edge areas 70 and 78, and no extra significant spikes have been discovered. FIG. 9B, however, discloses that one extra significant spike 104 near the left edge of the line profile was detected. This spike is to the left of the edge area 70 and is ignored by the algorithm as being on the free edge of the seal or is a detection of the longitudinal edge 22 (FIGS. 2 and 3) of the aligned gore sheets.

Figure 10A:
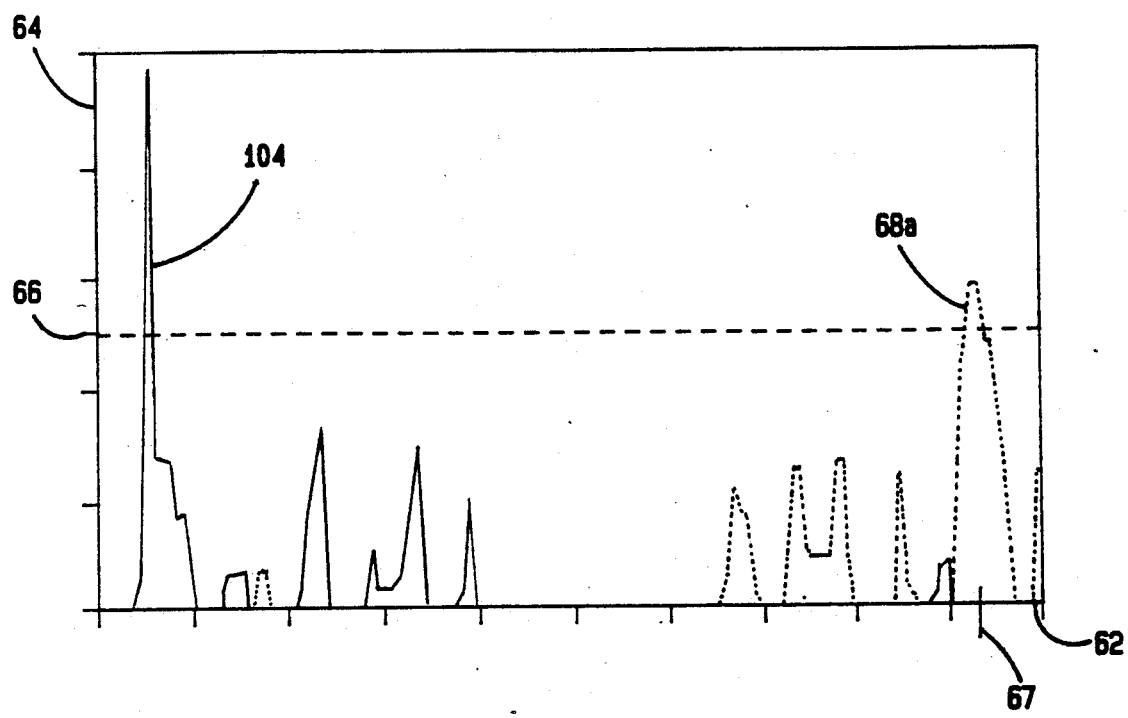
FIGS. 10A-10L show actual line profiles generated by the apparatus of the present invention showing a variety of flawed and defective seals.
Figure 10B:
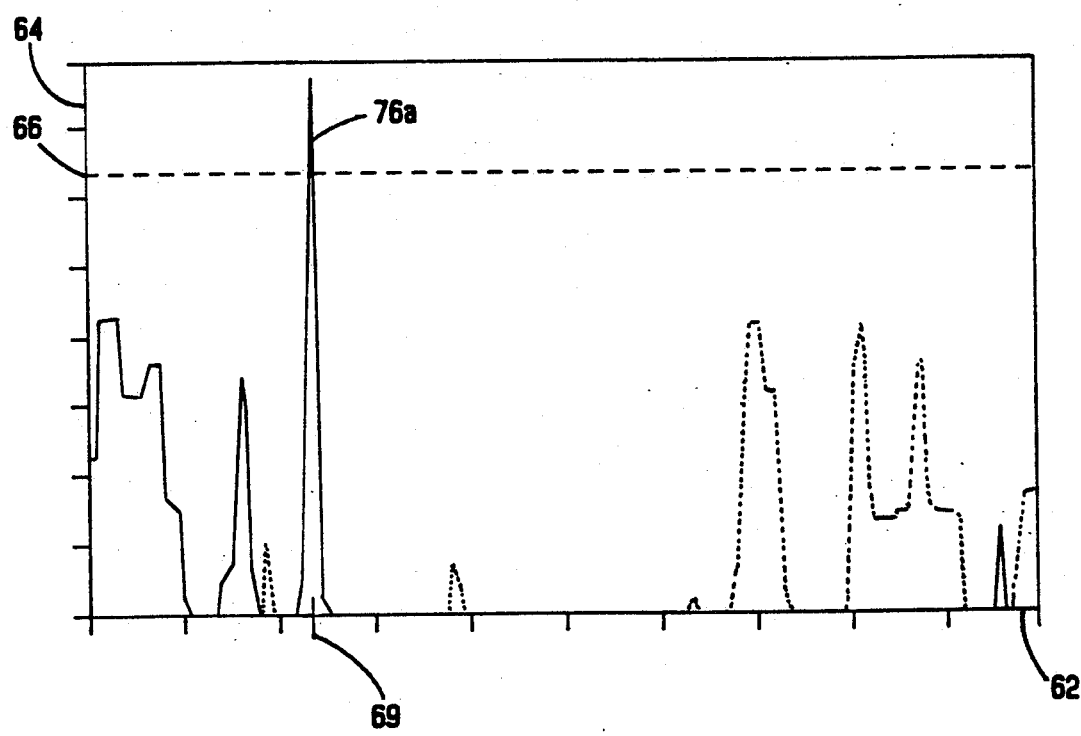
Figure 10C:
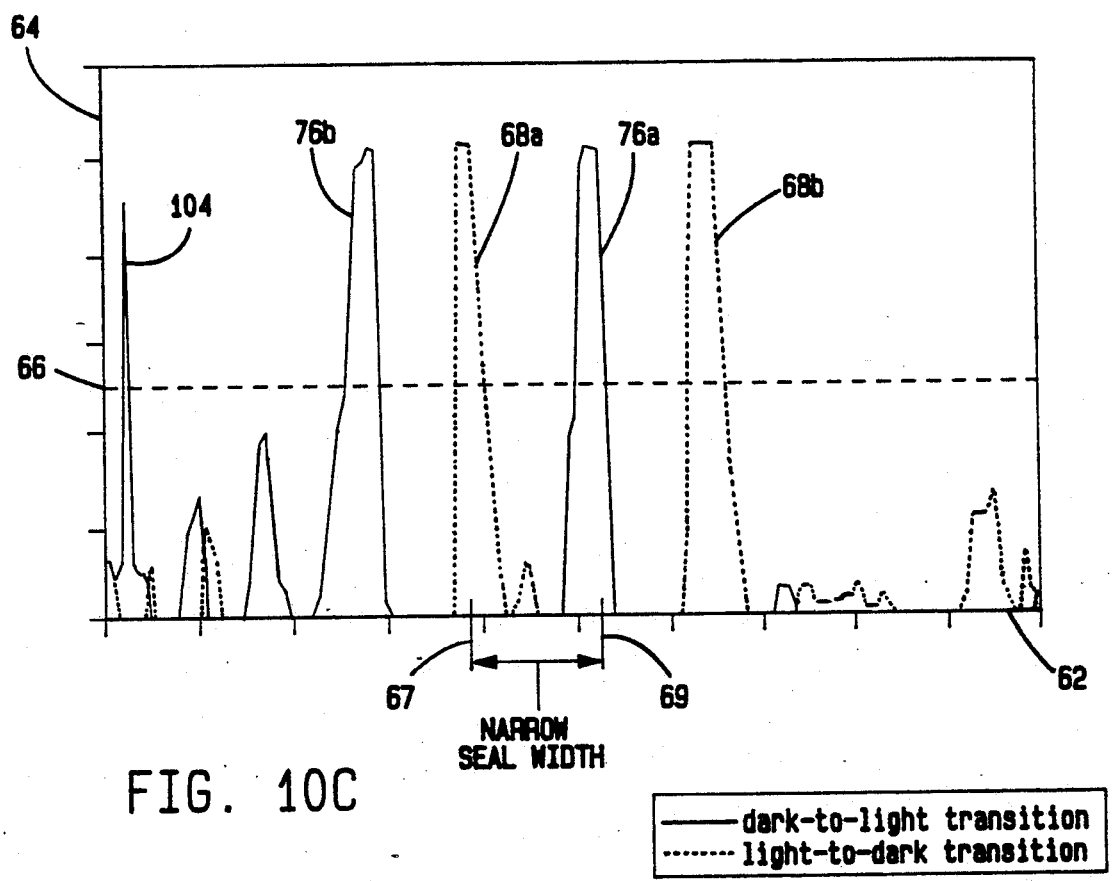

Referring now to FIGS. 10A-10L, there are shown several actual line profiles generated by the apparatus 40 for examined lateral sections of the heat seal in which the defect detection algorithm has identified a variety of included flaws and defects. Included flaws and defects are identified by the detection of narrow seal widths and extra seal edges. FIGS. 10A-10C are line profiles generated by the apparatus for a set of detected "cold" seals. Cold seals are characterized by seal widths less than the established one-eighth inch minimum value. From each generated profile it can be observed that the seal width is zero or relatively small. In FIG. 10A the first significant light-to-dark spike 68a indicating the location of the top edge 67 is detected, but no corresponding dark-to-light spike for the bottom edge is found. Thus, the seal width is zero and the seal is labeled as flawed. Similarly in FIG. 10B, no significant light-to-dark spike for the top edge is found to match the detected dark-to-light spike 76A for the bottom edge 69. In FIG. 10C, both the bottom edge 69 and the top edge 67 are detected, but the calculated seal width is relatively small thereby identifying a cold seal defect.

FIGS. 10D-10M are line profiles generated for all other anticipated flaw and defect types. FIG. 11D shows a line profile for a "tuck" flaw. Tuck flaws are the most commonly encountered flaw type and are generated when the gore layers or tapes fold or wrinkle in the seal. From the profile it is evident that both top and bottom edges, 67 and 69 respectively, are detected and that the seal width is within minimal standards. But an extra dominant dark-to-light spike 76d is detected near spike 76a outside edge area 78, thus indicating the existence of the flaw.

Figure 10D:
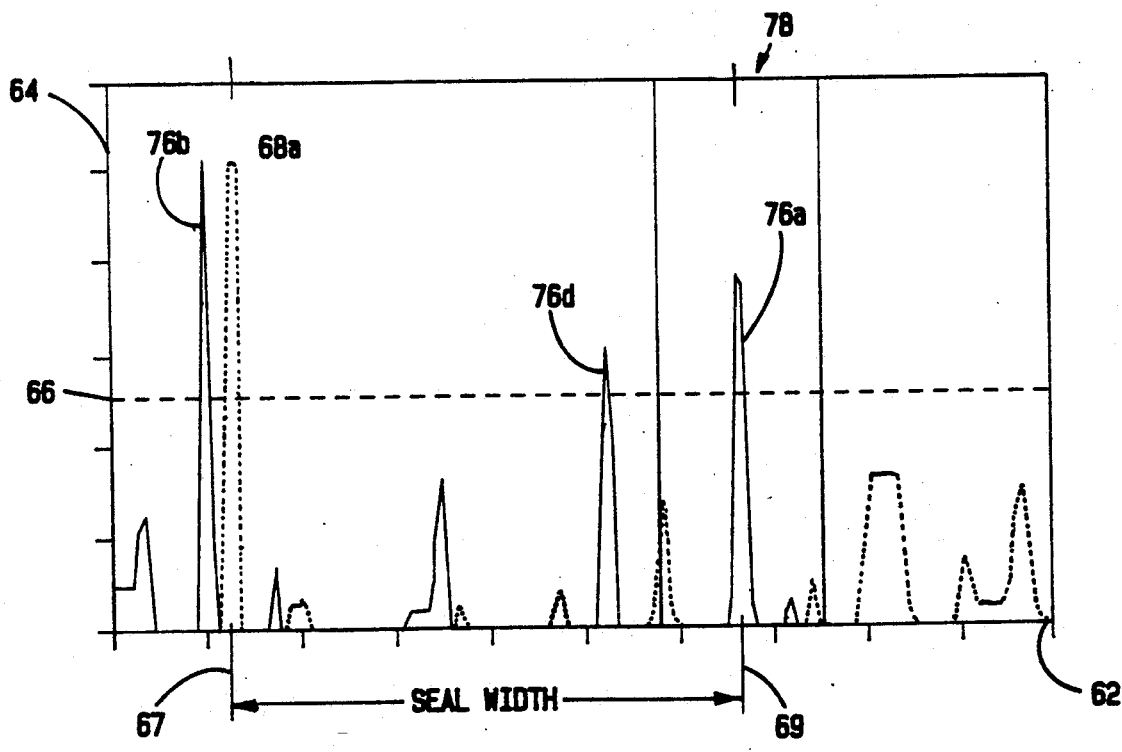
Figure 10E:
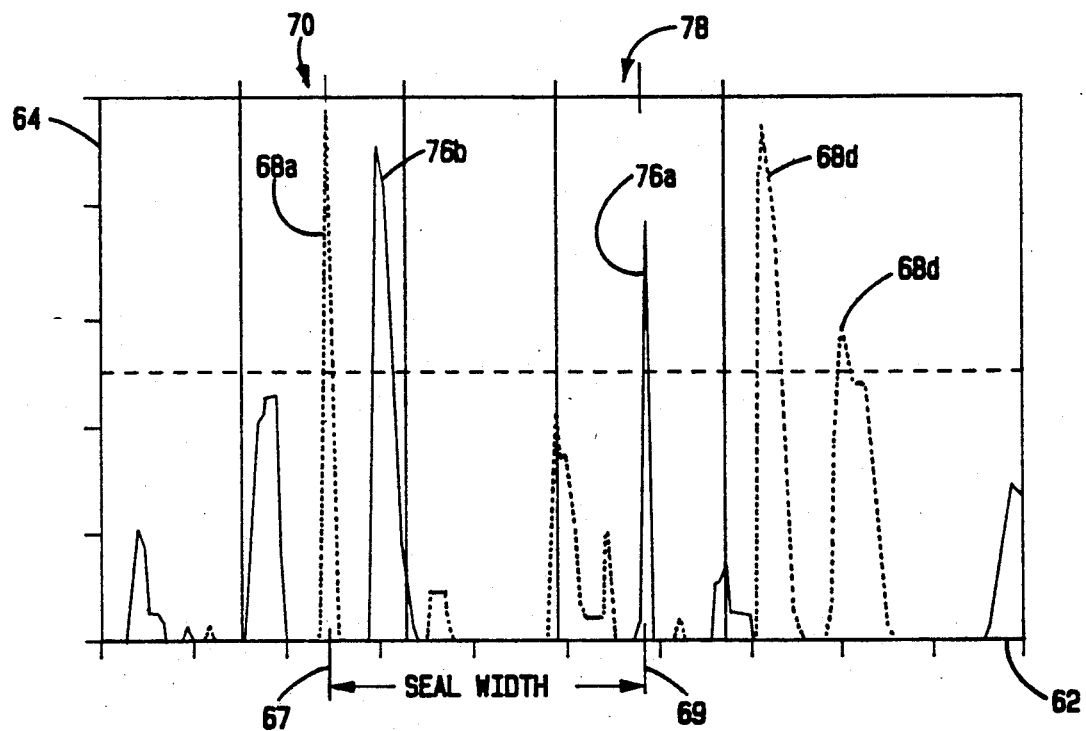
Figure 10F:
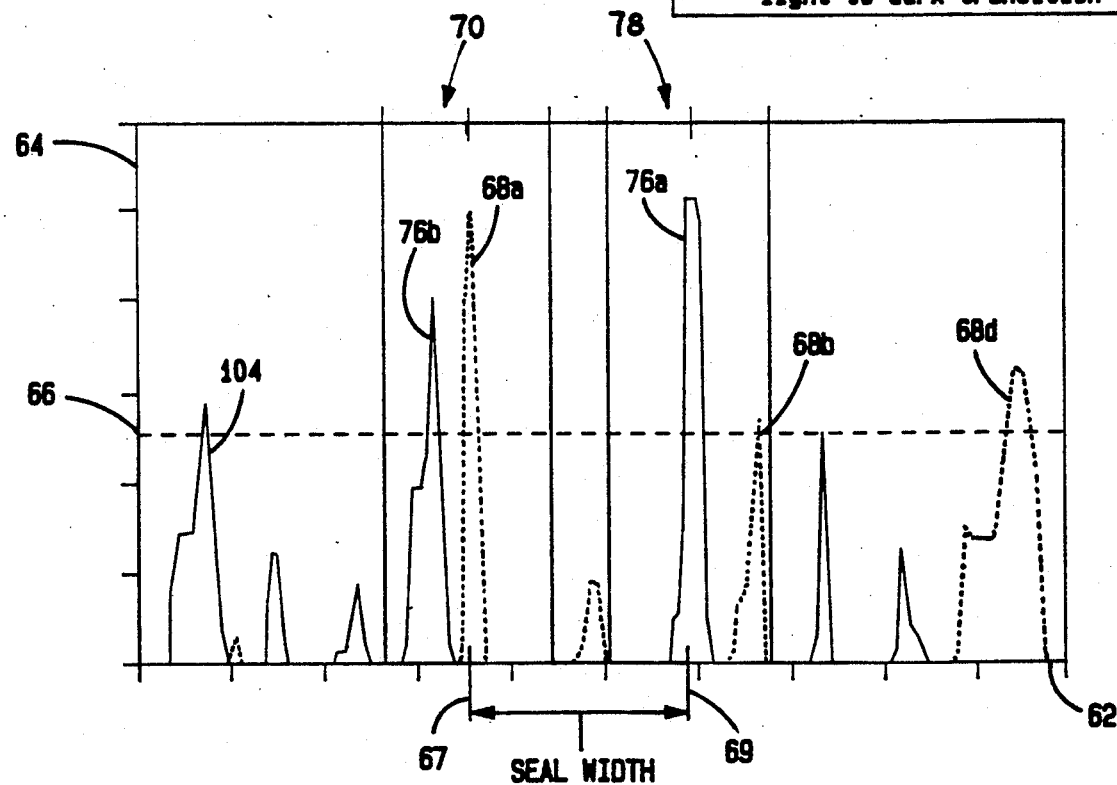
Figure 10G:
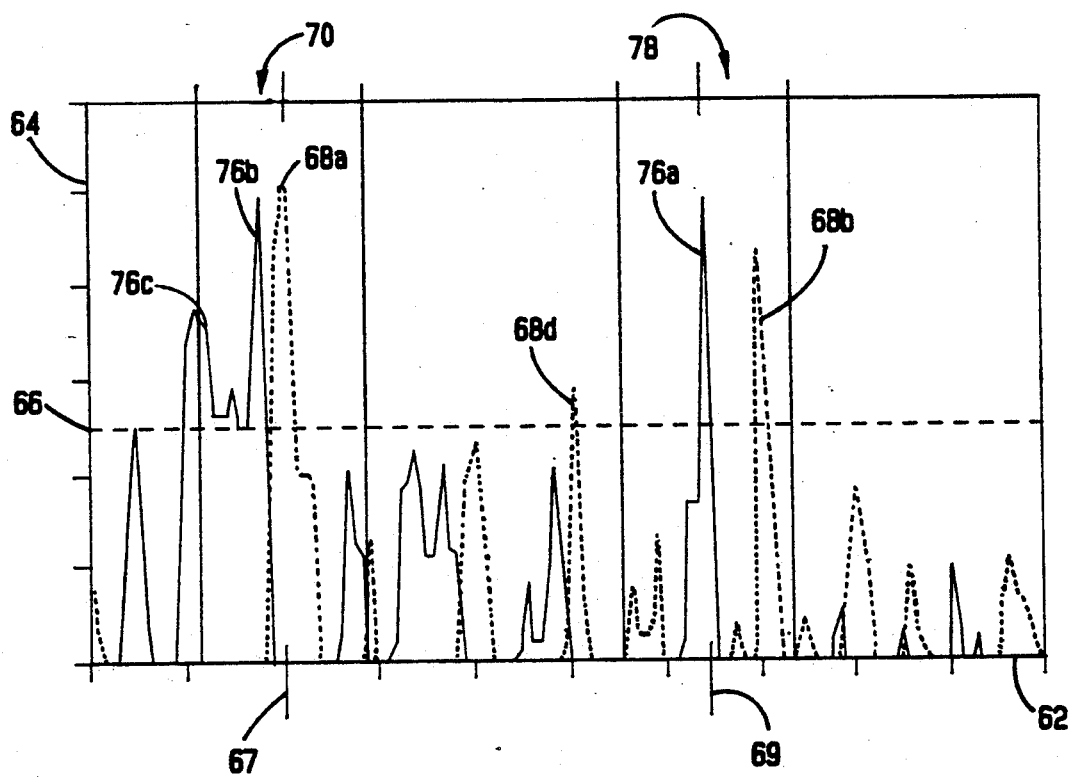

FIG. 10E shows a line profile for a "burned" seal defect. In a burned seal, the seal shrinks resulting in a smaller seal width and causes two extra significant light-to-dark spikes 68d to appear outside the bottom seal area 78. FIG. 10F shows a line profile generated for a seal section containing an included foreign object. A "debris" seal flaw profile is characterized by relatively small seal widths and the existence of extra dominant spikes. The line profile in FIG. 10F for a detected debris containing seal shows a narrow seal width, between top and bottom edges 67 and 69 respectively, and an extra significant light-to-dark spike 68d outside the bottom edge seal area 78. The line profile for a "saw-toothed" seal defect is shown in FIG. 10G. This seal defect is characterized by a wide seal width and the existence of an extra dominant spike 68d.

Figure 10H:
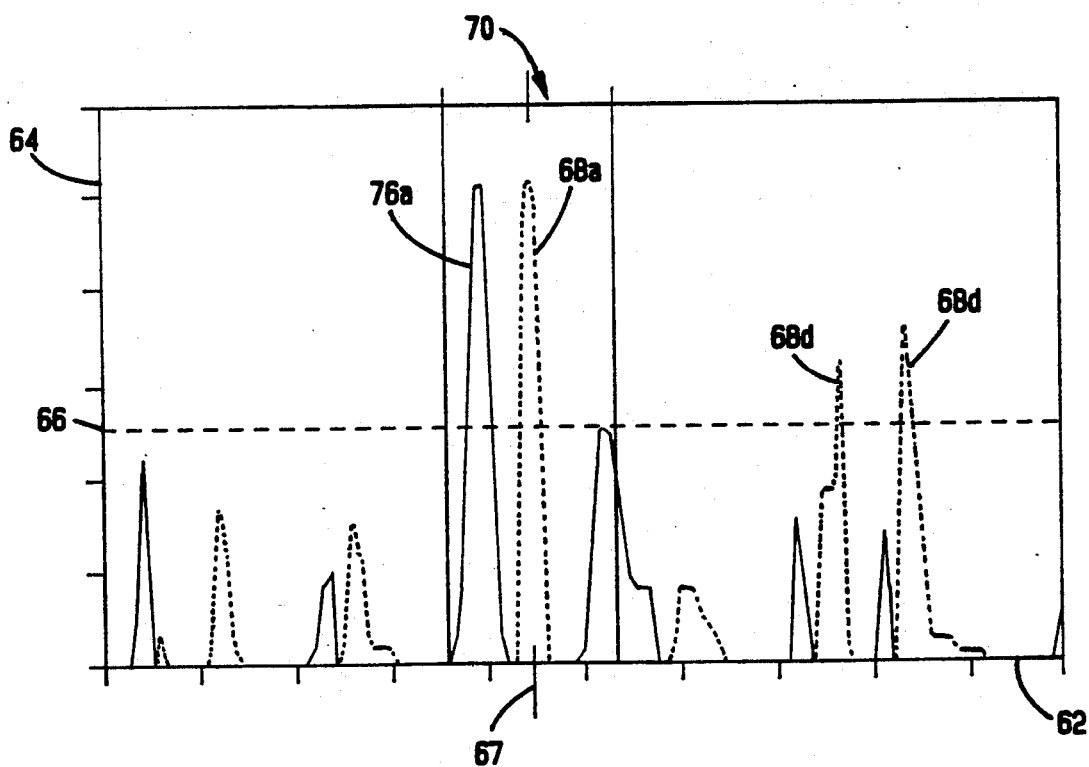
Figure 10I:
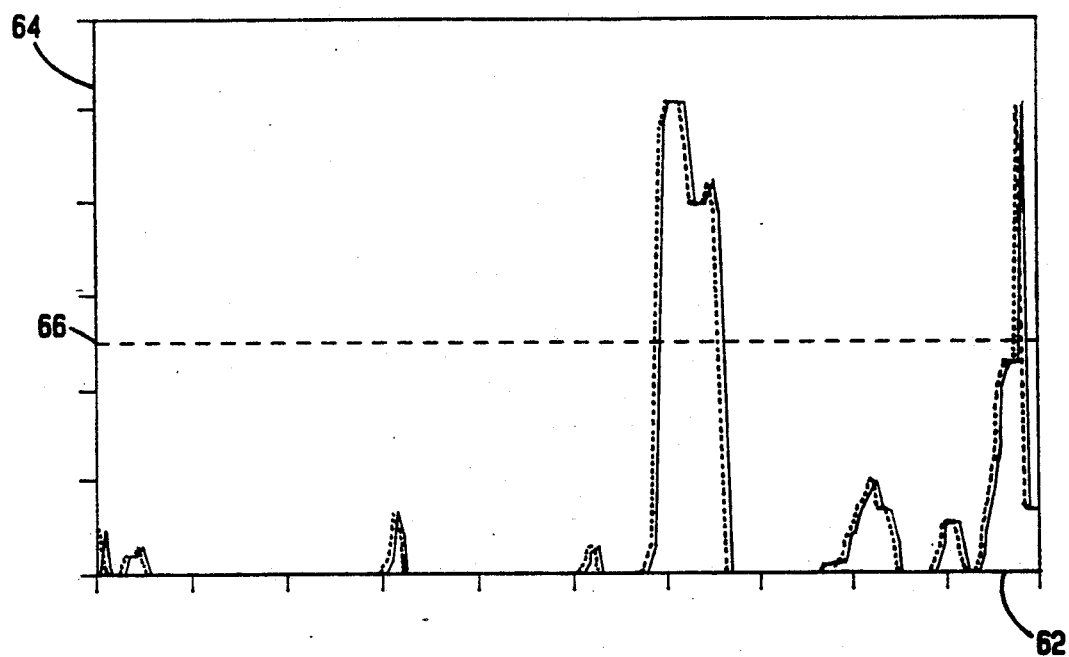

Defects in the seal can also exist when the load or backup tapes are not fully sealed to the balloon gores. A line profile for such a defect is shown in FIG. 10H. The top edge 67 has been detected by the presence of spike 68a, but no bottom edges present. Furthermore, a number of extra significant light-to-dark spikes, 68d, have also been detected outside the top edge area 70. Line profiles wherein the light-to-dark and dark-to-light spikes overlap as shown in FIG. 10I are generated when the load tape folds over the seal and will be labeled by the apparatus as a flaw.

Figure 10J:
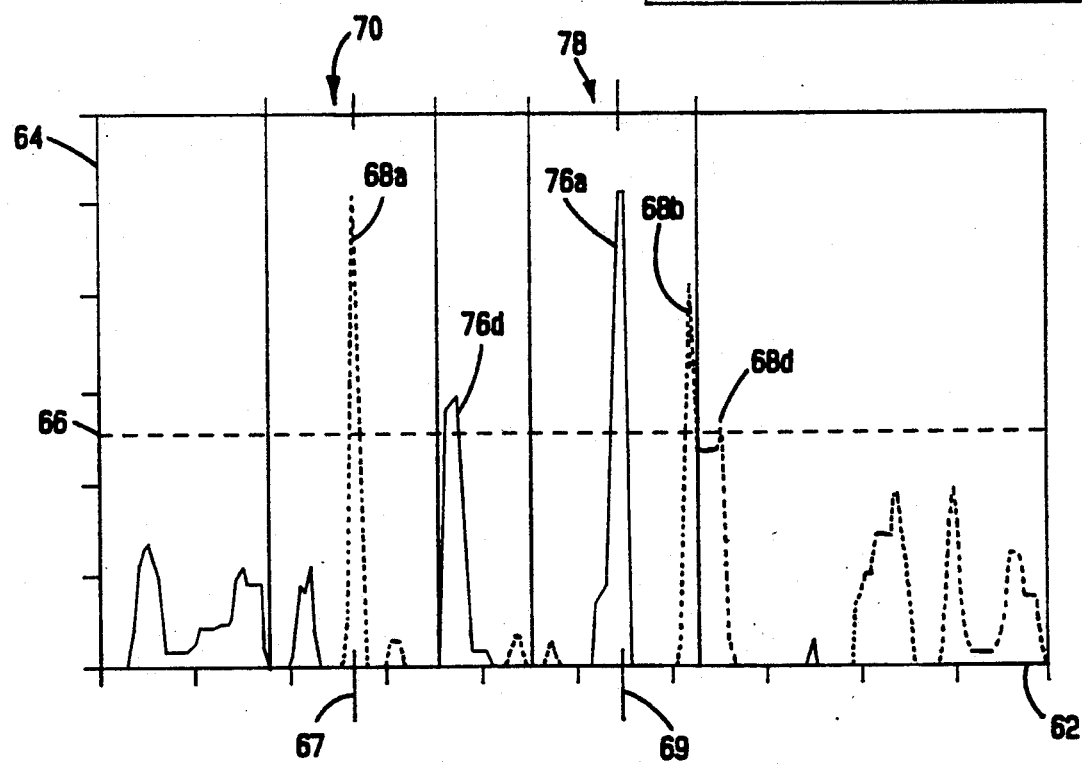

Another defect occurs when the seal width unexpectedly narrows. This type of flaw is called a "dip" in the seal. A line profile for a dip flaw is shown in FIG. 10J. The top edge 67 and bottom edge 69 are both detected, but the existence of an extra significant light-to-dark spike 68d and an extra dark-to-light spike 76d outside the top and bottom seal areas, 70 and 78 respectively, indicate the existence of an included dip flaw.

Figure 10K:
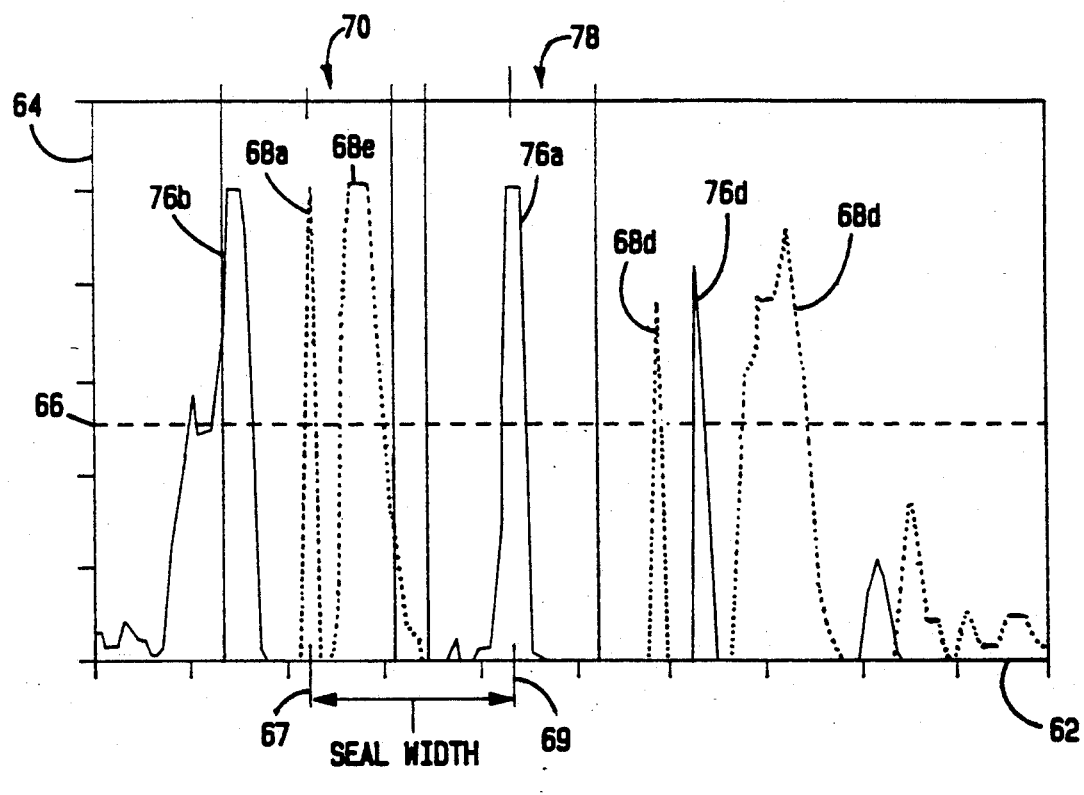
Figure 10L:
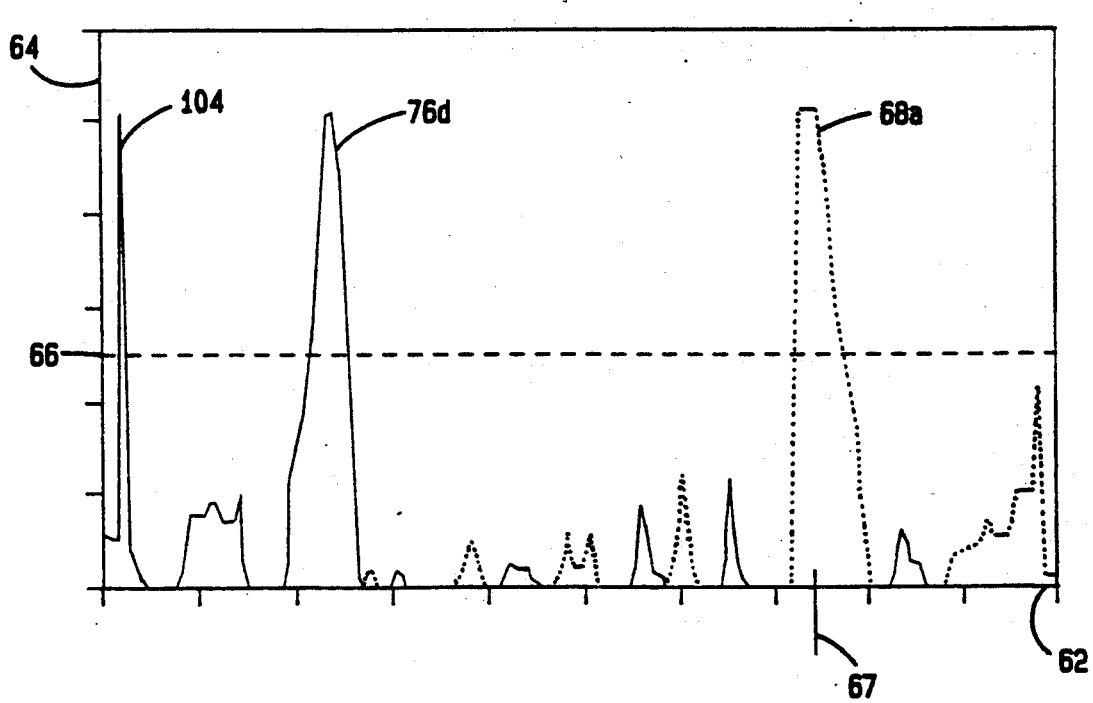

A "smear" in the seal occurs when one edge of the seal becomes distorted or thinned out. This defect is characterized by a line profile having a narrow seal width and a number of extra dominant spikes as shown in FIG. 10K including a double light-to-dark spike 68e. The line profile for a "cloudy" seal is shown in FIG. 10L. The top edge 67 has been located but no bottom edge to its right is found. In addition, a significant dark-to-light edge 76d is discovered.

Although the preferred embodiments for the invention have been illustrated in the accompanying Drawings and described in the foregoing Detailed Description, it will be understood that the invention is not limited to the embodiments disclosed, but is capable of numerous rearrangements and modifications of parts and elements without departing from the scope of the invention as defined by the following claims.

We claim:

1. A method for examining a heat seal formed between a plurality of translucent sheets to detect the presence of including flaws and defects, comprising the steps of:

transmitting electromagnetic radiation through a lateral section of the heat seal;

detecting the intensity of radiation transmitted through the lateral seal section;

generating a line profile for the lateral seal section, said line profile having a shape related to the integrity of the heat seal and an amplitude defined by changes in the detected radiation intensity across the lateral seal section;

processing the generated line profile to identify certain shape characteristics indicative of the integrity of the heat seal; and comparing the identified shape characteristics for the derived line profile with a predetermined line profile shape characteristic to detect the presence of a flaw or defect in the lateral seal section.

2. The method as in claim 1 wherein:

the step of processing includes the step of identifying a top and bottom edge characteristic for the heat seal from the shape of the line profile; and the step of comparing includes the steps of measuring the distance between the top and bottom edge characteristics and signalling a flaw in the lateral seal section if the measured distance is less than a standard edge distance for the predetermined line profile shape characteristic.

3. The method as in claim 1 wherein:

the step of processing includes the step of identifying a top and bottom edge area characteristic for the heat seal from the shape of the line profile; and the step of comparing includes the steps of locating instances in the line profile having an amplitude greater than a threshold amplitude and signalling a flaw in the lateral seal section if any portion of the line profile having an amplitude greater than the threshold amplitude is located outside the top or bottom seal edge area characteristics.

4. A method for detecting the presence of flaws and defects in a heat seal formed between a plurality of translucent sheets, comprising the steps of:

transmitting electromagnetic radiation through a lateral section of the heat seal;

detecting the intensity of the radiation transmitted through the lateral section of said heat seal;

generating a line profile for the lateral section having an amplitude related to changes across the lateral section in detected radiation intensity;

processing the changes in the amplitude of the generated line profile to identify the location each edge formed in the lateral section of the heat seal;

comparing the location and number of the identified heat seal edges to a preset location and number seal edge standard defined for a lateral section of a heat seal without a flaw or defect; and signalling a flaw or defect in the lateral section if the number of edges and edge locations do not correspond to the preset location and number seal edge standard.

5. The method as in claim 4 wherein the step of processing further includes the step of locating a top and a bottom edge for the lateral section of the heat seal.

6. The method as in claim 5 wherein the preset seal edge standard comprises a minimum distance between the located top and bottom edges and the step of comparing comprises the steps of:

measuring the distance between the located top and bottom edges; and comparing the measured distance against the minimum distance.

7. The method as in claim 4 wherein the step of processing further includes the step of locating a top, a bottom and other edge areas for the lateral section of the heat seal.

8. The method as in claim 7 wherein the preset seal edge standard comprises a prohibition against other edge areas located outside either the top or bottom edge areas and the step of comparing comprises the step of comparing the location of the other edge areas to the top and bottom edge areas.

9. A method for detecting the presence of flaws and defects in a heat seal formed between a plurality of translucent sheets, comprising the steps of:

defining predetermined shape characteristics for a heat seal line profile related to a heat seal without a flaw or defect;

transmitting electromagnetic radiation through a lateral section of the heat seal;

detecting the intensity of the radiation transmitted through the lateral section of said heat seal;

generating a line profile for the lateral section having a shape defined by the changes in detected radiation intensity;

identifying certain selected shape characteristics in the generated line profile; and comparing the selected shape characteristics of the generated line profile to the predetermined shape characteristics to detect the presence of an included flaw or defect in the lateral section of the seal.

10. The method as in claim 9 wherein the step of identifying certain selected shape characteristics comprised the step of identifying the changes in the shape of the line profile indicative of the presence of a top and bottom edge in the lateral section of the heat seal.

11. The method as in claim 10 wherein the predetermined shape characteristics comprise a preset location relationship between the top and bottom edges, and wherein the step of comparing comprises the step of measuring the distance between the shape characteristics for the top and bottom edges against the preset location relationship.

12. The method as in claim 11 wherein the preset location relationship comprises a minimum distance between the shape characteristics for the top and bottom edges in the lateral section of the heat seal.

13. A method for detecting the presence of flaws and defects in a heat seal formed between a a plurality of translucent sheets, comprising the steps of:

defining standard line profile spike characteristics relating to spike location and amplitude for a lateral section of a heat seal that does not contain a flaw or defect;

transmitting electromagnetic radiation through a lateral section of heat seal under examination;

measuring the intensity of the through transmitted electromagnetic radiation;

generating a line profile for the lateral section under examination having at least one spike, the line profile having an amplitude related to the measured intensity across the lateral section;

identifying certain heat seal spike characteristics from the generated line profile according to identified spike location and amplitude factors; and comparing the identified heat seal spike characteristics for the lateral section of heat seal under examination to the defined standard line profile spike characteristics to detect the presence of a flaw or defect.

14. An apparatus for examining a heat seal formed between a plurality of translucent sheets to detect the presence of flaws and defects comprising:

means for illuminating a lateral section of said heat seal;

means for detecting the intensity of radiation transmitted by said means for illuminating through the lateral section of sad heat seal;

means responsive to the detected intensity for generating a line profile for the lateral section having a shape related to the integrity of the heat seal and an amplitude proportional to the detected intensity across the lateral section;

means for processing the generated line profile to identify certain shape characteristics therein indicative of the integrity of the heat seal; and means for detecting the presence of flaws or defects by comparing the identified shape characteristics for the generated line profile with a predetermined line profile characteristic for a heat seal without a flaw or defect.

15. The apparatus as in claim 14 wherein the identified shape characteristics of the generated line profile include top and bottom seal edge characteristics and the means for detecting includes:

means for measuring the distance between a top and a bottom seal edge; and means for signalling a flaw in the lateral seal section if the measured distance does not correspond to a distance set by the predetermined line profile characteristic.

16. The apparatus as in claim 14 wherein the identified shape characteristics of the generated line profile include top and bottom edge area characteristics and the means for detecting includes:

means for identifying the location of a top and bottom edge area characteristic for the heat seal; and means for signalling a flaw in the lateral seal section if the amplitude of the line profile outside the top or bottom seal edge area characteristics exceeds a threshold set by the predetermined line profile characteristic.

17. Apparatus for examining a heat seal formed between a plurality of translucent sheets to detect the presence o flaws and defects comprising:
   means for illuminating a lateral section of the heat seal;
   means for detecting the intensity of illuminating through the lateral section;
   means for generating a line profile for the lateral section having an amplitude related to changes in the detected intensity across the lateral section;
   means for processing the changes in the amplitude of the generated line profile to identify the location of each edge formed in the lateral section of the heat seal;
   means for comparing the location and number of the identified heat seal edges to a preset location and number seal edge standard defined for a lateral section of a heat seal without a flaw or defect; and
   means for signalling a flaw or defect in the lateral section if the number of edges and edge locations do not correspond to the preset location and number seal edge standard.

18. The apparatus as in claim 17 wherein the means for processing includes means for locating a top and a bottom edge for the lateral section of the heat seal corresponding to certain changes in amplitude of the generated line profile.

19. The method as in claim 18 wherein the preset location and number seal edge standard comprises a minimum distance between the located top and bottom edges and the means for comparing comprises:
   means for measuring the distance between the located top and bottom edges; and
   means for comparing the measured distance against the minimum distance.

20. Apparatus for detecting the presence of flaws and defects in a heat seal formed between a plurality of translucent sheets, comprising:
   means for storing a predetermined shape characteristic for a heat seal line profile, the shape characteristic indicative of a heat seal without a flaw or defect;
   means for illuminating a lateral section of the heat seal;
   means for detecting the intensity of the illumination transmitted through the lateral section of said heat seal;
   means for generating a line profile for the lateral section having a shape defined by the changes in detected illumination intensity;
   means for identifying certain selected shape characteristics in the generated line profile; and
   means for comparing the selected shape characteristics of the generated line profile to the stored shape characteristics to detect the presence of an included flaw or defect in the lateral section of the seal.

21. The apparatus as in claim 20 wherein the means for identifying certain selected shape characteristics comprises means for identifying the changes in the shape of the line profile indicative of the presence of a top and bottom edge in the lateral section of the heat seal.

22. The apparatus as in claim 21 wherein the predetermined shape characteristics comprise a preset location relationship between the top and bottom edges, and wherein the means for comparing comprises means for measuring the distance between the shape characteristics for the top and bottom edges against the preset location relationship.

23. The apparatus as in claim 22 wherein the preset location relationship comprises a minimum distance between the shape characteristics for the top and bottom edges in the lateral section of the heat seal.

24. Apparatus for detecting the presence of flaws and defects in a heat seal formed between a plurality of translucent sheets, comprising:
   means for storing standard line profile spike characteristics relating to spike location and amplitude for a lateral section of a heat seal that does not contain a flaw or defect;
   means for transmitting electromagnetic radiation through a lateral section of heat seal under examination;
   means for measuring the intensity of the through transmitted electromagnetic radiation;
   means for generating a line profile for the lateral section under examination having at least one spike, the line profile having an amplitude related to the measured intensity across the lateral section;
   means for identifying certain heat seal characteristics from the generated line profile according to identified spike location and amplitude factors; and
   means for comparing the identified heat seal spike characteristics for the lateral section of heat seal under examination to the stored standard line profile spike characteristics to detect the presence of a flaw or defect.

* * * * *

UNITED STATES PATENT AND TRADEMARK OFFICE
CERTIFICATE OF CORRECTION

PATENT NO. : 5,184,190
DATED : Feb. 2, 1993
INVENTOR(S) : Kula R. Rai; Thomas M. Lew; Robert B. Sinclair It is certified that error appears in the above-identified patent and that said Letters Patent is hereby corrected as shown below:

Column 4, line 17, "sea" should be --seal--.

Column 6, line 42, "19 serve" should be --19 (FIG. 3) serve--.

Column 7, line 54, "transition" should be --transitions--.

Column 8, line 6, "sensor 42" should be --sensor 44--.

Column 9, line 24, "are" should be --area--.

Column 9, line 31, "70a" should be --76a--.

Column 10, line 5, "lenses 82" should be --lenses 28 and 82--.

Column 10, line 13, "photo electric" should be --photoelectric--.

Column 10, line 16, "array 94" should be --array 92--.

Column 11, line 26, "FIG. 11D" should be --FIG. 10D--.

Column 12, line 23, "including" should be --included--.

UNITED STATES PATENT AND TRADEMARK OFFICE
CERTIFICATE OF CORRECTION

PATENT NO. : 5,184,190
DATED : February 2, 1993
INVENTOR(S) : Kula R. Rai, et al.

It is certified that error appears in the above-indentified patent and that said Letters Patent is hereby corrected as shown below:

Column 14, line 35, "sad" should read --said--.

Signed and Sealed this

Twenty-sixth Day of April, 1994

Attest:

BRUCE LEHMAN

*Attesting Officer*   *Commissioner of Patents and Trademarks*